(12) United States Patent
Takeuchi

(10) Patent No.: US 11,549,111 B2
(45) Date of Patent: Jan. 10, 2023

(54) COMPOSITION FOR SUPPRESSING INFLAMMATION

(71) Applicant: Kyoto University, Kyoto (JP)

(72) Inventor: Osamu Takeuchi, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 16/981,763

(22) PCT Filed: Mar. 20, 2019

(86) PCT No.: PCT/JP2019/011851
§ 371 (c)(1),
(2) Date: Sep. 17, 2020

(87) PCT Pub. No.: WO2019/182055
PCT Pub. Date: Sep. 26, 2019

(65) Prior Publication Data
US 2021/0032630 A1    Feb. 4, 2021

(30) Foreign Application Priority Data

Mar. 22, 2018 (JP) .............................. JP2018-054780

(51) Int. Cl.
*C12N 15/113* (2010.01)
*A61P 11/00* (2006.01)
*A61P 37/02* (2006.01)
*C12Q 1/6897* (2018.01)

(52) U.S. Cl.
CPC .......... *C12N 15/1137* (2013.01); *A61P 11/00* (2018.01); *A61P 37/02* (2018.01); *C12Q 1/6897* (2013.01); *C12N 2310/11* (2013.01); *C12N 2310/3233* (2013.01)

(58) Field of Classification Search
CPC ............ C12N 15/1137; C12N 2310/11; C12N 2320/31; A61K 31/713; A61K 31/7088
See application file for complete search history.

(56) References Cited

FOREIGN PATENT DOCUMENTS

EP    3251693 A1    12/2017

OTHER PUBLICATIONS

Mino et al., Regnase-1 and Roquin Regulate a Common Element in Inflammatory mRNAs by Spatiotemporally Distinct Mechanisms, Cell 161: 1058-1073 (2015).
Iwasaki et al., "The IkB kinase complex regulates the stability of cytokine-encoding mRNA induced by TLR-IL-1R by controlling degradation of regnase-1," Nature Immunology, 12 (12): 1167-1175 (2011).
Makki et al., "HDAC Inhibitor SAHA Induces MCPIP1 Expression and Suppresses IL-6 Expression in Human OA Chondrocytes," Osteoarthritis and Cartilage, 233: A156 (2015).

(Continued)

*Primary Examiner* — Terra C Gibbs
(74) *Attorney, Agent, or Firm* — Morgan, Lewis & Bockius LLP

(57) ABSTRACT

The disclosure provides a composition for suppressing inflammation comprising at least one substance that disrupts a stem-loop structure in the 3' untranslated region of a Regnase-1 mRNA, wherein the stem-loop structure is at least one stem-loop structure selected from a first stem-loop structure formed in a region corresponding to positions 231 to 245 of SEQ ID NO: 1 and a second stem-loop structure formed in a region corresponding to positions 424 to 442 of SEQ ID NO: 1.

17 Claims, 10 Drawing Sheets
Specification includes a Sequence Listing.

```
SEQ ID NO: 3

1 MSGPCGEKPV LEASPTMSLW EFEDSHSRQG TPRPGQELAA EEASALELQM KVDFFRKLGY
 61 SSTEIHSVLQ KLGVQADTNT VLGELVKHGT ATERERQTSP DFCPQLPLVP RGGGTPKAPN
121 LEPPLPEEEK EGSDLRPVVI DGSNVAMSHG NKEVFSCRGI LLAVNWFLER GHTDITVFVP
181 SWRKEQPRPD VFITDQHILR ELEKKKILVF TPSRRVGGKR VVCYDDRFIV KLAYESDGIV
241 VSNDTYRDLQ GERQEWKRFI EERLLMYSFV NDKFMPPDDP LGRHGPSLDN FLRKKPLTLE
301 HRKQPCPYGR KCTYGIKCRF FHPERFSCPQ RSVADELRAN ALLSPFRAPS KDKNGRRFSP
361 SSQSSSLLTE SEQCSLDGKR LGAQASPGSR QEGLTQTYAF SGRSIAPSGG SGSSFGPTDW
421 LPQTLDSLPY VSQDCLDSGI GSLESQMSEL WGVRGGGPGE PGPPRAPYTG YSPYGSELPA
481 TAAFSAFGRA MGAGHFSVPA DYPPAPPAFP PREYWSEPYP LPPPTSVLQE PPVQSPGAGR
541 SPWGRAGSLA KEQASVYTKL CGVFPPHLVE AVMGRFPQLL DPQQLAAEIL SYKSQHPSE

SEQ ID NO: 4

1 MSDPCGTKPV QESNPTMSLW SLEDRHSSQG RPQFDQDPVA KEAPTSELQM KVDFFRKLGY
 61 SSSEIHSVLQ KLGVQADTNT VLGELVKHGS ATERECQALT APSPQPPLVP RGGSTPKPST
121 LEPSLPEEDR EGSDLRPVVI DGSNVAMSHG NKEVFSCRGI LLAVNWFLER GHTDITVFVP
181 SWRKEQPRPD VFITDQHILR ELEKKKILVF TPSRRVGGKR VVCYDDRFIV KLAFESDGVV
241 VSNDTYRDLQ GERQEWKRFI EERLLMYSFV NDKFMPPDDP LGRHGPSLDN FLRKKPLPSE
301 HRKQPCPYGK KCTYGIKCRF FHPERFSRPQ RSVADELRAN ALLSPPRTPV KDKSSQRFSP
361 ASQSSSVSLE AEPGSLDGKK LGARSSPGFH REGSPQTCAF AGRSLPVSGG SFGPTEWLAH
421 TQDSLPYTSQ ECLDSGIGSL ESQMSELWGV RGGSPGESGF TRGPYAGYHS YGSKVPAAPS
481 FSPFRPAMGA GHFSVPTDYV PPPPTYPSRE YWSEPYPLPF PTPVLQEPQR PSPGAGGPW
541 GRVGDLAKER AGVYTKLCGV FPPHLVEAVM RRFPQLLDPQ QLAAEILSYK SQHLSE
```

(56) References Cited

OTHER PUBLICATIONS

Mao et al., "Regnase-1, a rapid response ribonuclease regulating inflammation and stress responses," Cellular & Molecular Immunology, 14: 412-422 (2017).
Behrens et al., "A translational silencing function of MCPIP1/Regnase-1 specified by the target site context," Nucleic Acids Research, 46 (8): 4256-4270 (2018).
Wilamowski et al., "Substrate specificity of human MCPIP1 endoribonuclease," Scientific Reports, 8 (1): 7381 (2018).
International Search Report issued in corresponding International Patent Application No. PCT/JP2019/011851 dated Jun. 18, 2019.
International Preliminary Report on Patentability and Written Opinion issued in corresponding International Patent Application No. PCT/JP2019/011851 dated Oct. 1, 2020.
Extended European Search Report issued in corresponding European Patent Application No. 19772013.9 dated Feb. 24, 2022.

Fig. 1

SEQ ID NO: 3

```
  1 MSGPCGEKPV LEASPTMSLW EFEDSHSRQG TPRPGQELAA EEASALELQM KVDFFRKLGY
 61 SSTEIHSVLQ KLGVQADTNT VLGELVKHGT ATERERQTSP DPCPQLPLVP RGGGTPRAPN
121 LEPPLPEEEK EGSDLRPVVI DGSNVAMSHG NKEVFSCRGI LLAVNWFLER GHTDITVFVP
181 SWRKEQPRPD VPITDQHILR ELEKKKILVF TPSRRVGGKR VVCYDDRFIV KLAYESDGIV
241 VSNDTYRDLQ GERQEWKRFI EERLLMYSFV NDKFMPPDDP LGRHGPSLDN FLRKKPLTLE
301 HRKQPCPYGR KCTYGIKCRF FHPERPSCPQ RSVADELRAN ALLSPPRAPS KDKNGRRPSP
361 SSQSSSLLTE SEQCSLDGKK LGAQASPGSR QEGLTQTYAP SGRSLAPSGG SGSSFGPTDW
421 LPQTLDSLPY VSQDCLDSGI GSLESQMSEL WGVRGGGPGE PGPPRAPYTG YSPYGSELPA
481 TAAFSAFGRA MGAGHFSVPA DYPPAPFAFP PREYWSEPYP LPPPTSVLQE PFVQSPGAGR
541 SPWGRAGSLA KEQASVYTKL CGVFPPHLVE AVMGRFPQLL DPQQLAAEIL SYKSQHPSE
```

SEQ ID NO: 4

```
  1 MSDPCGTKPV QESNPTMSLW SLEDRHSSQG RPQPDQDPVA KEAPTSELQM KVDFFRKLGY
 61 SSSEIHSVLQ KLGVQADTNT VLGELVKHGS ATERECQALT APSPQPPLVP RGGSTPKPST
121 LEPSLPEEDR EGSDLRPVVI DGSNVAMSHG NKEVFSCRGI LLAVNWFLER GHTDITVFVP
181 SWRKEQPRPD VPITDQHILR ELERKKILVE EERLLMYSFV NDKFMPPDDP LGRHGPSLDN
241 VSNDTYRDLQ GERQEWKRFI EERLLMYSFV NDKFMPPDDP LGRHGPSLDN FLRKKPLPSE
301 HRKQPCPYGK KCTYGIKCRF FHPERPSRPQ RSVADELRAN ALLSPPRTPV KDKSSQRPSP
361 ASQSSSVSIE AEPGSLDGKK LGARSSPGPH REGSPQTCAP AGRSLPVSGG SFGPTEWLAH
421 TQDSLPYTSQ ECLDSGIGSL ESQMSELWGV RGGSPGESGP TRGPYAGYHS YGSKVPAAPS
481 FSPFRPAMGA GHFSVPTDIV PPPPTYPSRE YWSEPYPLPP PTPVLQEPQR PSPGAGGGPW
541 GRVGDLAKER AGVYTKLCGV FPPHLVEAVM RRFPQLLDPQ QLAAEILSYK SQHLSE
```

Fig. 2

```
gcugccugug gcuggcaagg gcagcacccc cagccuccaa gggccgucag gcugggcuuu    60
gggccauuga gcagcccauu cccagcccug aggcccaccc cagaggcugg acagagggag   120
gauucaaguc gggaaggaaa cccacaaacc aaagauacug uaggauuggu ucuggcccau   180 gcagcacccuc uagcugucug ccucagugggg ucagaagcga ucacccuguu gauacacauu   240
guaucucugu aguuuaagga gacgcugccg guaacggcgu cgguccgugg cugaggccca   300
binding site of 231-245 MO
aaccgucuuu ucucucagag gguggggagg gagguggggg cagcagaggc cugggcuggg   360
ugcccugugc acgccacccc acuuccgccc uaccccuggg acguuggccu uggcuggcua   420
guugggcacc gugugccugc ccuccaaggg ccuccucuac gccaaugagg cccaucugu    480
binding site of 424-442 MO                          ⊢— SEQ ID NO: 5
gcucucgcug ggcacguggc uucaugucag uaagcaagau gcuucuuaau aacccaccuu   540
cugccccacu cuauuccuua uccugcugcc ccguaggggg ucaagggccc uccgucuaca   600
cccucuucuu cucuccauc cuuuauucag agucaucucg cccuucccca ugggugggggg   660 aaccugugu uguuugugug cacauguaaa uuuuaaauau uuuaagcaga aagccuuac   720 cuccuguaac acaucaauaa aguacaauca uugugagccc uuuca              765
```

Human Regnase-1 mRNA 3' UTR (SEQ ID NO: 1)

Fig. 3

```
gccagaaggu ggcgcaaggg gcugucgggc aucacagaua gcggucccca gccccugccu    60
ggccuacccu ggaagcugga cagaaggaca agugaagcag gcaagggaau ccucaaacca   120
aagauaccau aggauugguu cuggccccgc ggcaccccaa cccgucccgc acaggucaga   180
                                                     SEQ ID NO: 6
agugaucacc cuguu gauac acauu guauc ucugucauuu aaggagacgc ugccggucag   240
                 binding site of 191-210 MO
gccguccauc cguggcugau gcccaaaccc ucuuuuuuuu uucucagagg gccggguggg   300
aggcaugggg gagcagaggc cugagcugga ccccaccuuc cacccugucc cugggacgcc   360
ggcaccaccg gcuaguu agg cac caug ugc cug cucucug aggcccccuc aagccaaugc   420
                 binding site of 378-392 MO
ggccucaucc cuguucacag ggcaugaggc uucauguuag uaagcaagau gcuucuuuaa   480
gccccucccc ugccgcucu guccaccuac acaccccccc cccaaccagg gcuccaaggc   540
ccucuguuuc cacaccuccc auggguggga ggacacaugu augcugugua cagaggcgag   600
auuuaaauau uuuaaaugaa aaagguugac aaaauaaagg cuauugccag gcaggcugga   660
gagauggcuc aguгgguuaag agcaccgacu gcucuucuga agguccugag uucaaauguc   720
agcaaccaca ugguggcuca caaacaucug ugaugagauc uggugcccuc uucuggggug   780
ucugaagaca gcuacagugu acuuacauac aauaauaaau cuuuuaaaaa agagagaaau   840
uuaaaagaaa aaaaaagcua uugcc                                          865
```

Mouse Regnase-1 mRNA 3' UTR (SEQ ID NO: 2)

Fig. 6
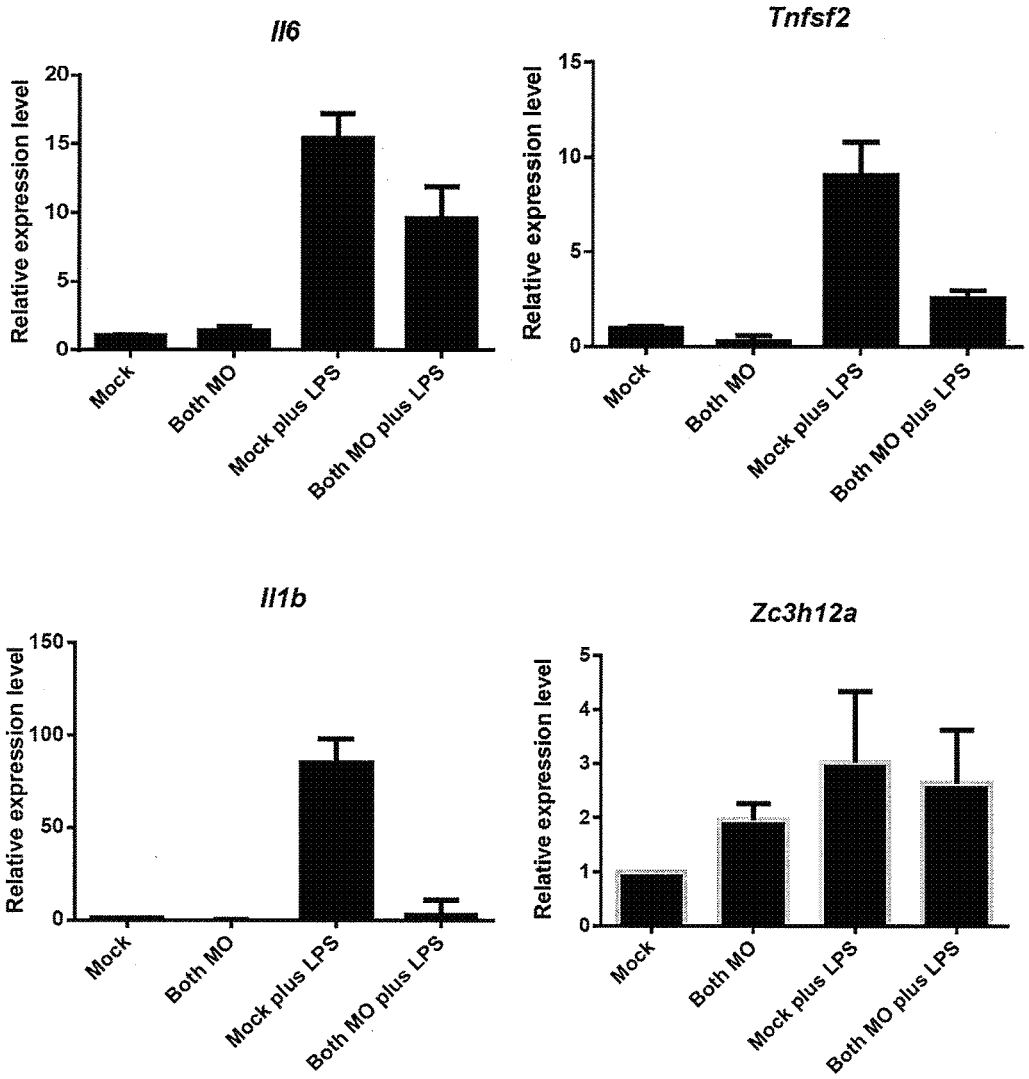
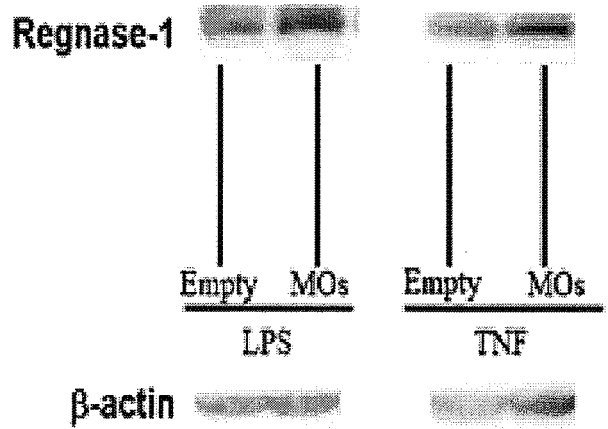

```
SEQUENCE LISTING

<160> NUMBER OF SEQ ID NOS: 16

<210> SEQ ID NO 1
<211> LENGTH: 765
<212> TYPE: RNA
<213> ORGANISM: Homo sapiens

<400> SEQUENCE: 1
gcugccugug gcuggcaagg gcagcacccc cagccuccaa gggccgucag gcugggcuuu      60
gggccauuga gcagcccauu cccagcccug aggcccaccc cagaggcugg acagagggag     120
gauucaaguc gggaaggaaa cccacaaacc aaagauacug uaggauuggu ucuggcccau     180
gcagcaccuc uagcugucug ccucaguggg ucagaagcga ucacccuguu gauacacauu     240
guaucucugu aguuuaagga gacgcugccg guaacggcgu cgguccgugg cugaggccca     300
aaccgucuuu ucucucagag ggugggagg gaggugggg cagcagaggc cugggcuggg     360
ugcccugugc acgccacccc acuuccgccc uaccccuggg acguuggccu uggcuggcua     420
guugggcacc gugugccugc ccuccaaggg ccuccucuac gccaaugagg ccucaucugu     480
gcucucgcug ggcacguggc uucaugucag uaagcaagau gcuucuuaau aacccaccuu     540
cugccccacu cuauuccuua uccugcugcc ccuguagggg ucaagggccc uccgucuaca     600
cccucuucuu cuccuccauc cuuuauucag agucaucucg cccuucccca uggguggggg     660
aaccuguguu uguuugugug cacauguaaa uuuuaaauau uuuaagcaga aaguccuuac     720
cuccuguaac acaucaauaa aguacaauca uugugagccc uuuca                     765

<210> SEQ ID NO 2
<211> LENGTH: 865
<212> TYPE: RNA
<213> ORGANISM: Mus musculus

<400> SEQUENCE: 2
gccagaaggu ggcgcaaggg gcugucgggc aucacagaua gcggucccca gccccugccu      60
ggccuacccu ggaagcugga cagaaggaca agugaagcag gcaagggaau ccucaaacca     120
aagauaccau aggauugguu cuggccccgc ggcacccaa cccgucccgc acaggucaga     180
agugaucacc cuguugauac acauuguauc ucugucauuu aaggagacgc ugccggucag     240
gccguccauc cguggcugau gcccaaaccc ucuuuuuuuu uucucagagg gccgggugg     300 aggcaugggg gagcagaggc cugagcugga ccccaccuuc cacccuguc cuggacgcc     360 ggcaccaccg gcuaguuagg caccauguge cugcucucug aggcccccuc aagccaaugc     420
ggccucaucc cuguucacag ggcaugaggc uucauguuag uaagcaagau gcuucuuuaa     480
```

```
gccccucccc ugcccgcucu guccaccuac acaccccccc cccaaccagg gcuccaaggc    540
ccucuguuuc cacaccuccc auggguggga ggacacaugu augcugugua cagaggcgag    600
auuuaaauau uuuaaaugaa aaagguugac aaaauaaagg cuauugccag gcaggcugga    660
gagauggcuc agugguuaag agcaccgacu gcucuucuga agguccugag uucaaaugus    720
agcaaccaca ugguggcuca caaacaucug ugaugagauc uggugcccuc uucggggug     780 ucugaagaca gcuacagugu acuuacauac aauaauaaau cuuuuaaaaa agagagaaau    840
uuaaaagaaa aaaaaagcua uugcc                                          865
```

```
<210> SEQ ID NO 3
<211> LENGTH: 599
<212> TYPE: PRT
<213> ORGANISM: Homo sapiens

<400> SEQUENCE: 3

Met Ser Gly Pro Cys Gly Glu Lys Pro Val Leu Glu Ala Ser Pro Thr
1               5                   10                  15

Met Ser Leu Trp Glu Phe Glu Asp Ser His Ser Arg Gln Gly Thr Pro
            20                  25                  30

Arg Pro Gly Gln Glu Leu Ala Ala Glu Glu Ala Ser Ala Leu Glu Leu
        35                  40                  45

Gln Met Lys Val Asp Phe Phe Arg Lys Leu Gly Tyr Ser Ser Thr Glu
    50                  55                  60

Ile His Ser Val Leu Gln Lys Leu Gly Val Gln Ala Asp Thr Asn Thr
65                  70                  75                  80

Val Leu Gly Glu Leu Val Lys His Gly Thr Ala Thr Glu Arg Glu Arg
                85                  90                  95

Gln Thr Ser Pro Asp Pro Cys Pro Gln Leu Pro Leu Val Pro Arg Gly
            100                 105                 110

Gly Gly Thr Pro Lys Ala Pro Asn Leu Glu Pro Pro Leu Pro Glu Glu
        115                 120                 125

Glu Lys Glu Gly Ser Asp Leu Arg Pro Val Val Ile Asp Gly Ser Asn
    130                 135                 140

Val Ala Met Ser His Gly Asn Lys Glu Val Phe Ser Cys Arg Gly Ile
145                 150                 155                 160

Leu Leu Ala Val Asn Trp Phe Leu Glu Arg Gly His Thr Asp Ile Thr
                165                 170                 175

Val Phe Val Pro Ser Trp Arg Lys Glu Gln Pro Arg Pro Asp Val Pro
            180                 185                 190

Ile Thr Asp Gln His Ile Leu Arg Glu Leu Glu Lys Lys Lys Ile Leu
        195                 200                 205

Val Phe Thr Pro Ser Arg Arg Val Gly Gly Lys Arg Val Val Cys Tyr
    210                 215                 220

Asp Asp Arg Phe Ile Val Lys Leu Ala Tyr Glu Ser Asp Gly Ile Val
225                 230                 235                 240

Val Ser Asn Asp Thr Tyr Arg Asp Leu Gln Gly Glu Arg Gln Glu Trp
                245                 250                 255

Lys Arg Phe Ile Glu Glu Arg Leu Leu Met Tyr Ser Phe Val Asn Asp
            260                 265                 270

Lys Phe Met Pro Pro Asp Asp Pro Leu Gly Arg His Gly Pro Ser Leu
        275                 280                 285

Asp Asn Phe Leu Arg Lys Lys Pro Leu Thr Leu Glu His Arg Lys Gln
    290                 295                 300
```

```
Pro Cys Pro Tyr Gly Arg Lys Cys Thr Tyr Gly Ile Lys Cys Arg Phe
305                 310                 315                 320

Phe His Pro Glu Arg Pro Ser Cys Pro Gln Arg Ser Val Ala Asp Glu
            325                 330                 335

Leu Arg Ala Asn Ala Leu Leu Ser Pro Arg Ala Pro Ser Lys Asp
        340                 345                 350

Lys Asn Gly Arg Arg Pro Ser Pro Ser Ser Gln Ser Ser Leu Leu
        355                 360                 365

Thr Glu Ser Glu Gln Cys Ser Leu Asp Gly Lys Lys Leu Gly Ala Gln
370                 375                 380

Ala Ser Pro Gly Ser Arg Gln Glu Gly Leu Thr Gln Thr Tyr Ala Pro
385                 390                 395                 400

Ser Gly Arg Ser Leu Ala Pro Ser Gly Gly Ser Gly Ser Ser Phe Gly
                405                 410                 415

Pro Thr Asp Trp Leu Pro Gln Thr Leu Asp Ser Leu Pro Tyr Val Ser
            420                 425                 430

Gln Asp Cys Leu Asp Ser Gly Ile Gly Ser Leu Glu Ser Gln Met Ser
        435                 440                 445

Glu Leu Trp Gly Val Arg Gly Gly Pro Gly Glu Pro Gly Pro Pro
450                 455                 460

Arg Ala Pro Tyr Thr Gly Tyr Ser Pro Tyr Gly Ser Glu Leu Pro Ala
465                 470                 475                 480

Thr Ala Ala Phe Ser Ala Phe Gly Arg Ala Met Gly Ala Gly His Phe
                485                 490                 495

Ser Val Pro Ala Asp Tyr Pro Pro Ala Pro Pro Ala Phe Pro Pro Arg
            500                 505                 510

Glu Tyr Trp Ser Glu Pro Tyr Pro Leu Pro Pro Thr Ser Val Leu
            515                 520                 525

Gln Glu Pro Pro Val Gln Ser Pro Gly Ala Gly Arg Ser Pro Trp Gly
530                 535                 540

Arg Ala Gly Ser Leu Ala Lys Glu Gln Ala Ser Val Tyr Thr Lys Leu
545                 550                 555                 560

Cys Gly Val Phe Pro Pro His Leu Val Glu Ala Val Met Gly Arg Phe
                565                 570                 575

Pro Gln Leu Leu Asp Pro Gln Gln Leu Ala Ala Glu Ile Leu Ser Tyr
        580                 585                 590

Lys Ser Gln His Pro Ser Glu
        595

<210> SEQ ID NO 4
<211> LENGTH: 596
<212> TYPE: PRT
<213> ORGANISM: Mus musculus

<400> SEQUENCE: 4

Met Ser Asp Pro Cys Gly Thr Lys Pro Val Gln Glu Ser Asn Pro Thr
1               5                   10                  15

Met Ser Leu Trp Ser Leu Glu Asp Arg His Ser Ser Gln Gly Arg Pro
            20                  25                  30

Gln Pro Asp Gln Asp Pro Val Ala Lys Glu Ala Pro Thr Ser Glu Leu
        35                  40                  45

Gln Met Lys Val Asp Phe Phe Arg Lys Leu Gly Tyr Ser Ser Ser Glu
50                  55                  60

Ile His Ser Val Leu Gln Lys Leu Gly Val Gln Ala Asp Thr Asn Thr
```

```
                65                   70                   75                   80
Val Leu Gly Glu Leu Val Lys His Gly Ser Ala Thr Glu Arg Glu Cys
                    85                   90                   95

Gln Ala Leu Thr Ala Pro Ser Pro Gln Pro Pro Leu Val Pro Arg Gly
                    100                  105                  110

Gly Ser Thr Pro Lys Pro Ser Thr Leu Glu Pro Ser Leu Pro Glu Glu
                    115                  120                  125

Asp Arg Glu Gly Ser Asp Leu Arg Pro Val Val Ile Asp Gly Ser Asn
                    130                  135                  140

Val Ala Met Ser His Gly Asn Lys Glu Val Phe Ser Cys Arg Gly Ile
145                      150                  155                  160

Leu Leu Ala Val Asn Trp Phe Leu Glu Arg Gly His Thr Asp Ile Thr
                    165                  170                  175

Val Phe Val Pro Ser Trp Arg Lys Glu Gln Pro Arg Pro Asp Val Pro
                    180                  185                  190

Ile Thr Asp Gln His Ile Leu Arg Glu Leu Glu Lys Lys Ile Leu
                    195                  200                  205

Val Phe Thr Pro Ser Arg Arg Val Gly Gly Lys Arg Val Val Cys Tyr
                    210                  215                  220

Asp Asp Arg Phe Ile Val Lys Leu Ala Phe Glu Ser Asp Gly Val Val
225                      230                  235                  240

Val Ser Asn Asp Thr Tyr Arg Asp Leu Gln Gly Glu Arg Gln Glu Trp
                    245                  250                  255

Lys Arg Phe Ile Glu Glu Arg Leu Leu Met Tyr Ser Phe Val Asn Asp
                    260                  265                  270

Lys Phe Met Pro Pro Asp Asp Pro Leu Gly Arg His Gly Pro Ser Leu
                    275                  280                  285

Asp Asn Phe Leu Arg Lys Lys Pro Leu Pro Ser Glu His Arg Lys Gln
                    290                  295                  300

Pro Cys Pro Tyr Gly Lys Lys Cys Thr Tyr Gly Ile Lys Cys Arg Phe
305                      310                  315                  320

Phe His Pro Glu Arg Pro Ser Arg Pro Gln Arg Ser Val Ala Asp Glu
                    325                  330                  335

Leu Arg Ala Asn Ala Leu Leu Ser Pro Arg Thr Pro Val Lys Asp
                    340                  345                  350

Lys Ser Ser Gln Arg Pro Ser Pro Ala Ser Gln Ser Ser Val Ser
                    355                  360                  365

Leu Glu Ala Glu Pro Gly Ser Leu Asp Gly Lys Lys Leu Gly Ala Arg
                    370                  375                  380

Ser Ser Pro Gly Pro His Arg Glu Gly Ser Pro Gln Thr Cys Ala Pro
385                      390                  395                  400

Ala Gly Arg Ser Leu Pro Val Ser Gly Ser Phe Gly Pro Thr Glu
                    405                  410                  415

Trp Leu Ala His Thr Gln Asp Ser Leu Pro Tyr Thr Ser Gln Glu Cys
                    420                  425                  430

Leu Asp Ser Gly Ile Gly Ser Leu Glu Ser Gln Met Ser Glu Leu Trp
                    435                  440                  445

Gly Val Arg Gly Gly Ser Pro Gly Glu Ser Gly Pro Thr Arg Gly Pro
                    450                  455                  460

Tyr Ala Gly Tyr His Ser Tyr Gly Ser Lys Val Pro Ala Ala Pro Ser
465                      470                  475                  480

Phe Ser Pro Phe Arg Pro Ala Met Gly Ala Gly His Phe Ser Val Pro
                    485                  490                  495
```

```
Thr Asp Tyr Val Pro Pro Pro Thr Tyr Pro Ser Arg Glu Tyr Trp
            500                 505                 510

Ser Glu Pro Tyr Pro Leu Pro Pro Thr Pro Val Leu Gln Glu Pro
            515                 520                 525

Gln Arg Pro Ser Pro Gly Ala Gly Gly Pro Trp Gly Arg Val Gly
            530                 535                 540

Asp Leu Ala Lys Glu Arg Ala Gly Val Tyr Thr Lys Leu Cys Gly Val
545                 550                 555                 560

Phe Pro Pro His Leu Val Glu Ala Val Met Arg Arg Phe Pro Gln Leu
                565                 570                 575

Leu Asp Pro Gln Gln Leu Ala Ala Glu Ile Leu Ser Tyr Lys Ser Gln
            580                 585                 590

His Leu Ser Glu
        595

<210> SEQ ID NO 5
<211> LENGTH: 262
<212> TYPE: RNA
<213> ORGANISM: Homo sapiens

<400> SEQUENCE: 5
gugggucaga agcgaucacc cuguugauac acauuguauc ucuguaguuu aaggagacgc    60
ugccgguaac ggcgucgguc cguggcugag gcccaaaccg ucuuucucu cagagggugg   120 ggagggaggu gggggcagca gaggccuggg cugggugccc ugugcacgcc accccacuuc   180
cgcccuaccc cugggacguu ggccuuggcu ggcuaguugg gcaccgugug ccugcccucc   240
aagggccucc ucuacgccaa ug                                            262

<210> SEQ ID NO 6
<211> LENGTH: 246
<212> TYPE: RNA
<213> ORGANISM: Mus musculus

<400> SEQUENCE: 6
acaggucaga agugaucacc cuguugauac acauuguauc ucugucauuu aaggagacgc    60
ugccggucag gccguccauc cguggcugau gcccaaaccc ucuuuuuuuu uucucagagg   120
gccggguggg aggcaugggg gagcagaggc cugagcugga ccccaccuuc cacccugucc   180
cugggacgcc ggcaccaccg gcuaguuagg caccaugugc cugcucucug aggccccuc   240 aagcca                                                              246

<210> SEQ ID NO 7
<211> LENGTH: 23
<212> TYPE: DNA
<213> ORGANISM: Homo sapiens

<400> SEQUENCE: 7
aatgtgtatc aacagggtga tcg                                            23

<210> SEQ ID NO 8
<211> LENGTH: 23
<212> TYPE: DNA
<213> ORGANISM: Homo sapiens

<400> SEQUENCE: 8
cttaaactac agagatacaa tgt                                            23
```

```
<210> SEQ ID NO 9
<211> LENGTH: 19
<212> TYPE: DNA
<213> ORGANISM: Homo sapiens

<400> SEQUENCE: 9
acggtgccca actagccag                                                  19

<210> SEQ ID NO 10
<211> LENGTH: 19
<212> TYPE: DNA
<213> ORGANISM: Homo sapiens

<400> SEQUENCE: 10
ggcccttgga gggcaggca                                                  19

<210> SEQ ID NO 11
<211> LENGTH: 23
<212> TYPE: DNA
<213> ORGANISM: Mus musculus

<400> SEQUENCE: 11
aatgtgtatc aacagggtga tca                                             23

<210> SEQ ID NO 12
<211> LENGTH: 23
<212> TYPE: DNA
<213> ORGANISM: Mus musculus

<400> SEQUENCE: 12
cttaaatgac agagatacaa tgt                                             23

<210> SEQ ID NO 13
<211> LENGTH: 20
<212> TYPE: DNA
<213> ORGANISM: Mus musculus

<400> SEQUENCE: 13
atggtgccta actagccggt                                                 20

<210> SEQ ID NO 14
<211> LENGTH: 20
<212> TYPE: DNA
<213> ORGANISM: Mus musculus

<400> SEQUENCE: 14
cctcagagag caggcacatg                                                 20

<210> SEQ ID NO 15
<211> LENGTH: 21
<212> TYPE: RNA
<213> ORGANISM: Mus musculus

<400> SEQUENCE: 15
cuguugauac acauuguauc u                                               21

<210> SEQ ID NO 16
<211> LENGTH: 15
<212> TYPE: RNA
<213> ORGANISM: Mus musculus

<400> SEQUENCE: 16
aggcaccaug ugccu                                                      15
```

COMPOSITION FOR SUPPRESSING INFLAMMATION

A computer readable text file, entitled "SequenceListing.txt," created on or about Sep. 16, 2020 with a file size of about 15 kb contains the sequence listing for this application and is hereby incorporated by reference in its entirety.

TECHNICAL FIELD

This application claims the benefit of priority of Japanese Patent Application No. 2018-054780, the entire contents of which are incorporated herein by reference.

The disclosure relates to a composition for suppressing inflammation.

BACKGROUND

Inflammation is involved in many diseases and plays an important role especially in septic shock and autoimmune diseases. Therapies for acute respiratory distress syndrome (ARDS), a severe symptom of septic shock, are poorly available, except for steroid therapy. Recently developed therapies for autoimmune diseases include, for example, use of methotrexate, an immunosuppressant, for treating chronic rheumatoid arthritis, and antibody therapies targeting cytokines such as TNF, IL-6 receptors, and IL-1 receptors. However, some patients do no respond to anti-cytokine antibodies and antibody therapies are not effective to many autoimmune diseases such as systemic lupus erythematosus. Although type I interferon is known to be effective to multiple sclerosis, the efficacy is insufficient.

Regnase-1, also called Reg1, Zc3h12a, or Mcpip1, is a ribonuclease that suppresses excessive immune responses in the innate immune system by degrading mRNAs encoding molecules involved in inflammation induction and proinflammatory cytokines, e.g., interleukin (IL)-6, in immune cells such as macrophages and dendritic cells. Regnase-1 also suppresses excessive T cell activation in the acquired immune system by degrading mRNAs encoding molecules involved in the T cell activation.

Regnase-1 recognizes a stem-loop structure in the 3' untranslated region (3' UTR) of a translationally active target mRNA and degrades the mRNA (Non-Patent Literature 1). It is also known that Regnase-1 mRNAs have one stem-loop structure and are recognized and degraded by Regnase-1 itself (Non-Patent Literature 2).

REFERENCES

Non-Patent Literature

[Non-Patent Literature 1] Mino, T. et al., Cell 161, 1058-1073 (2015)
[Non-Patent Literature 2] Iwasaki H., Takeuchi O. et al., Nat Immunol. 12, 1167-1175 (2011)

SUMMARY

An object of the disclosure is to provide a novel agent for suppressing inflammatory.

The inventor has found that the 3' UTR of a Regnase-1 mRNA has two stem-loop structures conserved among species and that disruption of the stem-loop structures suppresses the Regnase-1-mediated degradation of the Regnase-1 mRNA and increases the amount of Regnase-1. Since Regnase-1 degrades mRNAs of proinflammatory cytokines, the increase of Regnase-1 results in suppression of inflammation.

Accordingly, an aspect of the disclosure provides a composition for suppressing inflammation comprising at least one substance that disrupts a stem-loop structure in the 3' untranslated region of a Regnase-1 mRNA.

Another aspect of the disclosure provides a method of screening for an agent for suppressing inflammation comprising
(a) introducing a candidate substance to a cell expressing a Regnase-1 gene and a reporter gene, the reporter gene fused with the 3' untranslated region of a Regnase-1 mRNA;
(b) measuring an expression level of the reporter gene in the cell, and
(c) identifying the candidate substance as the agent for suppressing inflammation when the expression level measured in the presence of the candidate substance is higher than the expression level measured in the absence of the candidate substance.

The disclosure allows suppressing inflammation by activating Regnase-1 in a subject. The disclosure also allows screening for an agent for suppressing inflammation by using regulation of gene expression by the 3' untranslated region of a Regnase-1 mRNA as an indicator.

BRIEF DESCRIPTION OF DRAWINGS

FIG. 1 shows the representative amino acid sequences of human and mouse Regnase-1.

FIG. 2 shows the representative nucleotide sequence of the 3' untranslated region of a human Regnase-1 mRNA (SEQ ID NO: 1). The regions capable of forming stem-loop structures are surrounded by solid lines and the regions capable of forming the loop portions of the stem-loop structures are shown in italics. The nucleotide sequences to which 231-245MO and 424-442MO bind are underlined. The nucleotide sequence at positions 206 to 467 of SEQ ID NO: 1 (SEQ ID NO: 5) is surrounded by dashed lines.

FIG. 3 shows the representative nucleotide sequence of the 3' untranslated region of a mouse Regnase-1 mRNA (SEQ ID NO: 2). The regions capable of forming the stem-loop structures are surrounded by solid lines and the regions capable of forming the loop portions of the stem-loop structures are shown in italics. The nucleotide sequences to which 191-210MO and 378-392MO bind are underlined. The nucleotide sequence at positions 171 to 416 of SEQ ID NO: 2 (SEQ ID NO: 6) is surrounded by dashed lines.

FIG. 6 shows the mRNA levels of the cytokines and Regnase-1 and the amount of Regnase-1 after LPS treatment in mouse bone marrow macrophages (BMMs) treated with MOs.

DETAILED DESCRIPTION

Figure 4:
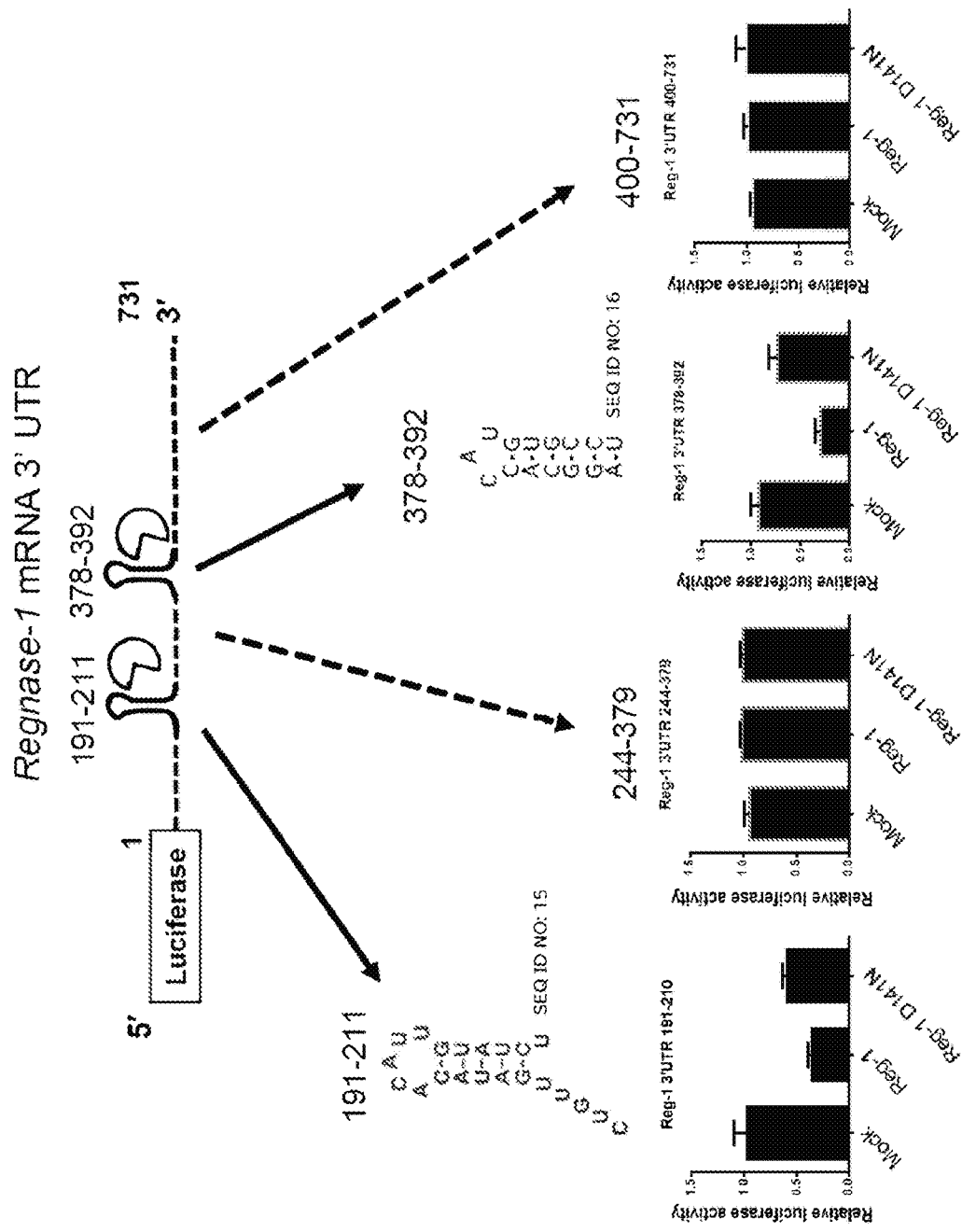
FIG. 4 shows a schematic drawing of the reporter construct used in Example 1 and the results of the reporter assay.

When a numerical value is accompanied with the term "about", the value is intended to represent any value in the range of −10% of the value to +10% of the value. For example, "about 20" means "a value from 18 to 22." A range defined with a value of the lower limit and a value of the upper limit covers all values from the lower limit to the upper limit, including the values of the both limits. When a numerical range is accompanied with the term "about", the both limits are read as accompanied with the term. For example, "about 20 to 30" is read as "18 to 33."

Unless otherwise defined, the terms used herein are read as generally understood by those skilled in the technical fields such as organic chemistry, medical sciences, pharmaceutical sciences, molecular biology, and microbiology. Several terms used herein are defined as below. The definitions herein take precedence over the general understanding.

The inventor has found that Regnase-1 recognizes two stem-loop structures located at the 3' UTR of a Regnase-1 mRNA and degrades the mRNA. In the Examples disclosed herein disruption of one or both of the stem-loop structures suppressed the degradation of the Regnase-1 mRNA and thus increased the amount of Regnase-1 and enhanced degradation of mRNAs of pro-inflammatory cytokines targeted by Regnase-1, such as IL-6, TNFα, and IL-1β. The degradation was similarly enhanced in an in vivo model. The results indicate that disruption of stem-loop structures at the 3' UTR of a Regnase-1 mRNA can suppress inflammation.

Regnase-1 may be of any species, typically a mammal, e.g., human, mouse, rat, hamster, rabbit, cat, dog, cow, sheep, or monkey, particularly human or mouse. The representative amino acid sequences of Regnase-1 are registered with GenBank accession numbers NP_001310479.1 (human, SEQ ID NO: 3) and NP_694799.1 (mouse, SEQ ID NO: 4). The term "Regnase-1" as used herein includes proteins having at least about 60%, about 70%, about 80%, about 85%, about 90%, about 95%, about 96%, about 97%, about 98%, or about 99% identity with the amino acid sequence of SEQ ID NO: 3 or 4, as long as they maintain the function of Regnase-1.

The term "3' untranslated region of a Regnase-1 mRNA" or "3' UTR of a Regnase-1 mRNA" means the region at the 3' end of the Regnase-1 mRNA that is not translated. The Regnase-1 mRNA as used herein may be any mRNA that comprises a nucleotide sequence encoding Regnase-1 as defined above, and may have any nucleotide sequence at the 3' untranslated region. Examples of the nucleotide sequences of the 3' UTRs include sequences comprising at least the sequence of SEQ ID NO: 5 (human) or SEQ ID NO: 6 (mouse). For example, the 3' UTR of a Regnase-1 mRNA comprises the nucleotide sequence shown in SEQ ID NO: 1 (human) or SEQ ID NO: 2 (mouse). In an embodiment, the 3' UTR of a Regnase-1 mRNA comprises a nucleotide sequence having at least about 60%, about 70%, about 80%, about 85%, about 90%, about 95%, about 96%, about 97%, about 98%, or about 99% identity with the nucleotide sequence of SEQ ID NO: 1, 2, 5, or 6.

In the disclosure the term "identity" of amino acid or nucleotide sequences means the degree of the similarity in sequences of proteins or oligonucleotides. The identity is determined by comparing two sequences that are optimally aligned with each other over the regions to be compared. The term "optimally aligned" means two sequences are aligned so that the number of the matched amino acids or nucleotides is maximized. The percentage (%) of the sequence identity is calculated by identifying the amino acids or nucleotides matched in the both sequences, determining the number of the matched amino acids or nucleotides, dividing the number by the total number of the amino acids or nucleotides in the regions to be compared, and multiplying the derived value by 100. For making the optimal alignment and calculating the sequence identity, any algorithm that is commonly available to those skilled in the art, e.g., BLAST algorithm or FASTA algorithm, may be used. The sequence identity may be determined using a software for sequence analysis such as BLAST or FASTA.

The term "stem-loop structure" means a structure in a single-stranded nucleic acid that is composed of a stem portion, which is formed by complementary binding of two sequences located at two separate regions of the nucleic acid, and a loop portion, which is formed by the region located between the two regions. In an embodiment, the stem-loop structure is a first stem-loop structure formed in a region corresponding to positions 231 to 245 of SEQ ID NO: 1 (human) and/or a second stem-loop structure formed in a region corresponding to positions 424 to 442 of SEQ ID NO: 1 in the 3' untranslated region of a Regnase-1 mRNA. In an embodiment, the stem-loop structure is a first stem-loop structure formed in a region corresponding to positions 196 to 210 of SEQ ID NO: 2 (mouse) and/or a second stem-loop structure formed in a region corresponding to positions 378 to 392 of SEQ ID NO: 2 in the 3' untranslated region of a Regnase-1 mRNA.

In the disclosure, when two nucleotide sequences are optimally aligned, a region in the second sequence that is aligned along a given region in the first sequence is defined as the region corresponding to the region in the first sequence.

The term "substance that disrupts a stem-loop structure" may be any substance that inhibits complementary binding within the stem-loop structure. Any substance that inhibits complementary binding of at least one, two, or three nucleotide pairs may be used. Examples of the substances include an oligonucleotide that binds to a nucleotide sequence forming a stem-loop structure (antisense nucleic acid), or a substance that modifies a nucleotide sequence forming a stem-loop structure via genome editing.

In an embodiment, the substance that disrupts a stem-loop structure is an antisense nucleic acid. The antisense nucleic acid may inhibit complementary binding within a stem-loop structure by binding to at least one portion of the region forming the stem-loop structure in the 3' untranslated region of a Regnase-1 mRNA, e.g., at least one, two, or three nucleotides forming the stem portion of the stem-loop structure. For example, the antisense nucleic acid comprises the sequence complimentary to a sequence comprising at least two or three, e.g., three, contiguous nucleotides that form the stem portion of a stem-loop structure. The contiguous nucleotides may be adjacent to the loop portion of the stem-loop structure. For example, the contiguous nucleotides may correspond to positions 233 to 235, 241 to 243, 426 to 428, and 438 to 440 of SEQ ID NO: 1. Preferably, the antisense nucleic acid does not form a stem-loop structure, a hairpin structure, or a multimer such as a dimer, by itself.

The antisense nucleic acid is a single-stranded nucleic acid consisting of, for example, 10 to 30, 15 to 27, 18 to 25, or 20 to 23 nucleotides.

In an embodiment, the antisense nucleic acid is selected from (a-1) an oligonucleotide consisting of 10 to 30 nucleotides and being capable of binding to a sequence that consists of contiguous 10 to 30 nucleotides within positions 206 to 242 of SEQ ID NO: 1 and comprises the nucleotides at positions 233 to 235 of SEQ ID NO: 1, and (a-2) an oligonucleotide consisting of 10 to 30 nucleotides and being capable of binding to a sequence that consists of contiguous 10 to 30 nucleotides within positions 234 to 270 of SEQ ID NO: 1 and comprises the nucleotides at positions 241 to 243 of SEQ ID NO: 1.

In an embodiment, the oligonucleotide (a-1) has at least about 60%, about 70%, about 80%, about 85%, about 90%, about 95%, about 96%, about 97%, about 98%, or about 99% sequence identity with SEQ ID NO: 7 (5'-AATGTGTATCAACAGGGTGATCG-3'). In another embodiment, the oligonucleotide (a-1) consists of a nucleotide sequence that is different from the nucleotide sequence of SEQ ID NO: 7 in that one or several, e.g., two or three, nucleotides are deleted, substituted, added, or inserted. In an embodiment, the oligonucleotide (a-1) has a nucleotide sequence having at least about 90% identity with SEQ ID NO: 7. In an embodiment, the oligonucleotide (a-1) comprises the nucleotide sequence of SEQ ID NO: 7. In an embodiment, the oligonucleotide (a-1) consists of the nucleotide sequence of SEQ ID NO: 7.

In an embodiment, the oligonucleotide (a-2) has at least about 60%, about 70%, about 80%, about 85%, about 90%, about 95%, about 96%, about 97%, about 98%, or about 99% sequence identity with SEQ ID NO: 8 (5'-CTTAAAC-TACAGAGATACAATGT-3'). In another embodiment, the oligonucleotide (a-2) consists of a nucleotide sequence that is different from the nucleotide sequence of SEQ ID NO: 8 in that one or several, e.g., two or three, nucleotides are deleted, substituted, added, or inserted. In an embodiment, the oligonucleotide (a-2) has a nucleotide sequence having at least about 90% identity with SEQ ID NO: 8. In an embodiment, the oligonucleotide (a-2) comprises the nucleotide sequence of SEQ ID NO: 8. In an embodiment, the oligonucleotide (a-2) consists of the nucleotide sequence of SEQ ID NO: 8.

In an embodiment, the antisense nucleic acid is selected from (b-1) an oligonucleotide consisting of 10 to 30 nucleotides and being capable of binding to a sequence that consists of contiguous 10 to 30 nucleotides within positions 399 to 439 of SEQ ID NO: 1 and comprises the nucleotides at positions 426 to 428 of SEQ ID NO: 1, and (b-2) an oligonucleotide consisting of 10 to 30 nucleotides and being capable of binding to a sequence that consists of contiguous 10 to 30 nucleotides within positions 427 to 467 of SEQ ID NO: 1 and comprises the nucleotides at positions 438 to 440 of SEQ ID NO: 1.

In an embodiment, the oligonucleotide (b-1) has at least about 60%, about 70%, about 80%, about 85%, about 90%, about 95%, about 96%, about 97%, about 98%, or about 99% sequence identity with SEQ ID NO: 9 (5'-ACGGTGCCCAACTAGCCAG-3'). In another embodiment, the oligonucleotide (b-1) consists of a nucleotide sequence that is different from the nucleotide sequence of SEQ ID NO: 9 in that one or several, e.g., two or three, nucleotides are deleted, substituted, added, or inserted. In an embodiment, the oligonucleotide (b-1) has a nucleotide sequence having at least about 90% identity with SEQ ID NO: 9. In an embodiment, the oligonucleotide (b-1) comprises the nucleotide sequence of SEQ ID NO: 9. In an embodiment, the oligonucleotide (b-1) consists of the nucleotide sequence of SEQ ID NO: 9.

In an embodiment, the oligonucleotide (b-2) has at least about 60%, about 70%, about 80%, about 85%, about 90%, about 95%, about 96%, about 97%, about 98%, or about 99% sequence identity with SEQ ID NO: 10 (5'-GGCCCTTGGAGGGCAGGCA-3'). In another embodiment, the oligonucleotide (b-2) consists of a nucleotide sequence that is different from the nucleotide sequence of SEQ ID NO: 10 in that one or several, e.g., two or three, nucleotides are deleted, substituted, added, or inserted. In an embodiment, the oligonucleotide (b-2) has a nucleotide sequence having at least about 90% identity with SEQ ID NO: 10. In an embodiment, the oligonucleotide (b-2) comprises the nucleotide sequence of SEQ ID NO: 10. In an embodiment, the oligonucleotide (b-2) consists of the nucleotide sequence of SEQ ID NO: 10.

The composition for suppressing inflammation may comprise one or more antisense nucleic acids. When two or more antisense nucleic acids are used, a composition containing all antisense nucleic acids may be used, or two or more compositions each containing one or more antisense nucleic acids may be used in combination. When a composition contains two or more antisense nucleic acids, the antisense nucleic acids preferably do not form a complementary bond between them. In an embodiment, a combination of one antisense nucleic acid selected from (a-1) and (a-2) and one antisense nucleic acid selected from (b-1) and (b-2) is used. For example, the combination of the antisense nucleic acids (a-1) and (b-1), the combination of the antisense nucleic acids (a-1) and (b-2), the combination of the antisense nucleic acids (a-2) and (b-1), or the combination of the antisense nucleic acids (a-2) and (b-2) is used.

In an embodiment, the antisense nucleic acid is selected from (a-1') an oligonucleotide consisting of 10 to 30 nucleotides and being capable of binding to a sequence that consists of contiguous 10 to 30 nucleotides within positions 171 to 207 of SEQ ID NO: 2 and comprises the nucleotides at positions 198 to 200 of SEQ ID NO: 2, and (a-2') an oligonucleotide consisting of 10 to 30 nucleotides and being capable of binding to a sequence that consists of contiguous 10 to 30 nucleotides within positions 199 to 235 of SEQ ID NO: 2 and comprises the nucleotides at positions 206 to 208 of SEQ ID NO: 2.

In an embodiment, the antisense nucleic acid is selected from (b-1') an oligonucleotide consisting of 10 to 30 nucleotides and being capable of binding to a sequence that consists of contiguous 10 to 30 nucleotides within positions 354 to 388 of SEQ ID NO: 2 and comprises the nucleotides at positions 381 to 383 of SEQ ID NO: 2, and (b-2') an oligonucleotide consisting of 10 to 30 nucleotides and being capable of binding to a sequence that consists of contiguous 10 to 30 nucleotides within positions 382 to 416 of SEQ ID NO: 2 and comprises the nucleotides at positions 387 to 389 of SEQ ID NO: 2.

The antisense nucleic acids (a-1'), (a-2'), (b-1'), and (b-2') are defined in accordance with the antisense nucleic acids (a-1), (a-2), (b-1), and (b-2) as described above.

In an embodiment, the oligonucleotides (a-1'), (a-2'), (b-1'), and (b-2') have at least about 60%, about 70%, about 80%, about 85%, about 90%, about 95%, about 96%, about 97%, about 98%, or about 99% sequence identity with SEQ ID NO: 11 (5'-aatgtgtatcaacagggtgatca-3'), SEQ ID NO: 12 (5'-cttaaatgacagagatacaatgt-3'), SEQ ID NO: 13 (5'-atggtgcctaactagccggt-3'), SEQ ID NO: 14 (5'-cctcagagagcaggcacatg-3'), respectively. In another embodiment, the oligonucleotides (a-1'), (a-2'), (b-1'), and (b-2') consist of a nucleotide sequence that is different from the nucleotide sequence of SEQ ID NOs: 11, 12, 13, and 14, respectively, in that one or several, e.g., two or three, nucleotides are deleted, substituted, added, or inserted. In an embodiment, the oligonucleotides (a-1'), (a-2'), (b-1'), and (b-2') have a nucleotide sequence having at least about 90% identity with SEQ ID NOs: 10, 11, 12, 13, and 14, respectively. In an embodiment, the oligonucleotides (a-1'), (a-2'), (b-1'), and (b-2') comprise the nucleotide sequence of SEQ ID NOs: 11, 12, 13, and 14, respectively. In an embodiment, the oligonucleotides (a-1'), (a-2'), (b-1'), and (b-2') consist of the nucleotide sequence of SEQ ID NOs: 11, 12, 13, and 14, respectively.

The antisense nucleic acid may be composed of natural nucleotides, or composed of artificial nucleotides, or composed of one or more natural nucleotides and one or more artificial nucleotides. Examples of the natural nucleotides include deoxyribonucleotides and ribonucleotides. The artificial nucleotides as used herein may have structures different from those of the natural nucleotides and increase the nuclease resistance or binding affinity with the target sequence of the antisense nucleic acid. For example, the artificial nucleotides as used herein include those described in Deleavey, G. F., & Damha, M. J. (2012). Designing chemically modified oligonucleotides for targeted gene silencing. Chemistry & biology, 19(8), 937-954, the entire contents of which are incorporated herein by reference. Examples of the artificial nucleotides include abasic nucleosides; arabinonucleosides, 2'-deoxyuridine, α-deoxyribonucleosides, β-L-deoxyribonucleosides, and nucleosides having any other sugar modification; peptide nucleic acids (PNAs), phosphonic ester nucleic acids (PHONAs), locked nucleic acids (LNAs), 2'-O,4'-C-ethylene-bridged nucleic acids (ENAs), constrained ethyl (cEt) nucleosides, and morpholino nucleic acids. Examples of the artificial nucleotides having sugar modifications include those having substituted pentoses such as 2'-o-methylribose, 2'-o-methoxyethylribose, 2'-deoxy-2'-fluororibose, or 3'-o-methylribose; 1',2'-deoxyribose; arabinose; substituted arabinoses; hexoses, and alpha-anomers. Examples of the artificial nucleotides having modified bases include those having pyrimidines such as 5-hydroxycytosine, 5-methylcytosine, 5-fluorouracil, or 4-thiouracil; purines such as 6-methyladenine or 6-thioguanosine; and other heterocyclic bases. The antisense nucleic acid may comprise artificial nucleotides of the same type or two or more different types.

In an embodiment, the antisense nucleic acid is a morpholino oligo. The morpholino oligo has a structure in which the following component is repeatedly linked.

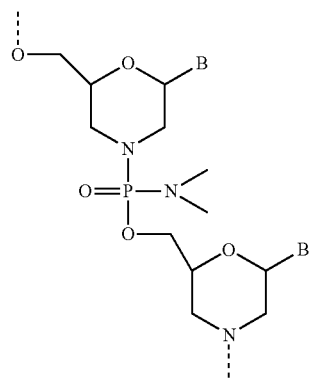

wherein B is adenine, cytosine, guanine, or thymine, and the dashed line is the point connected with the adjacent component.

In an embodiment, the antisense nucleic acid is a single-stranded DNA.

The antisense nucleic acid may be bound to one or more components or conjugates that enhance the activity or cellular uptake of the antisense nucleic acid. Such components may include, but are not limited to, cholesterol components, cholic acid, thioethers, e.g., hexyl-S-tritylthiols, thiocholesterol, aliphatic chains, e.g., dodecanediol or undecyl residues, phospholipids, e.g. di-hexadecyl-rac-glycerol or tri-ethylammonium 1,2-di-O-hexadecyl-rac-glycero-3-H-phosphonate, polyamine or polyethylene glycol chains, or adamantane acetic acid, palmitic components, or octadecylamine, hexylamino-carbonyl-t-oxycoresterol, or oct-aguanidine dendrimer components. Oligonucleotides containing such components and methods of preparing such oligonucleotides are known in the art.

The composition disclosed herein can suppress inflammation and thus can be used for treating and/or preventing a disease associated with inflammation. Diseases associated with inflammation include, for example, septic shock, autoimmune diseases, and graft rejection. Septic shock includes, for example, acute respiratory distress syndrome (ARDS), idiopathic pulmonary fibrosis, and interstitial pneumonia, especially acute respiratory distress syndrome. The autoimmune diseases include, for example, multiple sclerosis, autoimmune encephalomyelitis, rheumatoid arthritis, and systemic lupus erythematosus, especially multiple sclerosis.

The term "treating" or "treatment" as used herein means that in a subject suffering from a disease a cause of the disease is reduced or removed, progression of the disease is delayed or stopped, and/or a symptom of the disease is reduced, alleviated, ameliorated, or removed.

The term "preventing" or "prevention" as used herein means that in a subject, especially a subject that is susceptible to a disease but has not been affected with the disease yet, the disease onset is prevented or the possibility of the disease onset is decreased, wherein the disease onset includes recurrence of the disease. Examples of the subjects that are susceptible to septic shock but have not been affected with it yet include subjects suspected to be infected with bacteria, especially drug-resistant bacteria, subjects suffering from bacteremia, subjects having defects of heart valves, and subjects using or having medical devices such as catheters, tubes, artificial joints, or artificial heart valves in the bodies. Examples of the subjects that are susceptible to an autoimmune disease but have not been affected with it yet include subjects having genetic predispositions to the autoimmune disease.

The subjects of the treatment or prevention include animals, typically mammals (e.g., humans, mice, rats, hamsters, rabbits, cats, dogs, cows, sheep, or monkeys), especially humans.

The administration routes of the composition include oral or parenteral routes and are not particularly limited. Various known dosage forms may be employed depending on the application site and the target disease. For example, the parenteral administration may be systemic or local administration, more specifically, intratracheal, intraspinal, intrathecal, intracranial, intravenous, intraarterial, intraportal, intradermal, subcutaneous, intramuscular, intraperitoneal, intranasal, or intraoral administration. In an embodiment, the composition is administered intravenously. In an embodiment, the composition is administered intratracheally. In an embodiment, the composition is administered intrathecally, intraspinally, or intracranially.

Dosage forms such as granules, fine granules, powders, coated tablets, tablets, suppositories, fine powders, capsules, microcapsules, chewable tablets, liquids, suspensions, and emulsions may be employed. Dosage forms that prolong the release of the active ingredient may be employed. Dosage forms for injection or infusion include aqueous and non-aqueous injectable solutions, which may comprise an excipient, such as an antioxidant, a buffer, a bacteriostatic agent, or an isotonic agent; and aqueous and non-aqueous injectable suspensions, which may comprise an excipient, such as a suspending agent or thickening agent. Such dosage forms may be provided as liquids in sealed ampoules or vials, or provided as lyophilized products and prepared immediately prior to use by adding sterile liquids such as water for injection. The injectable solutions or suspensions may be prepared from powders, granules, or tablets.

Such dosage forms can be manufactured by formulating an active ingredient by conventional methods. If necessary for the formulation, any one of various pharmaceutically acceptable excipients may be added. Any excipient may be used in accordance with the employed dosage form. Examples of the excipients include buffering agents, surfactants, stabilizers, preservatives, fillers, diluents, additives, disintegrants, binders, coating agents, lubricants, lubricating agents, flavoring agents, sweeteners, and solubilizers.

The dosage and the number of doses of the composition may be appropriately set by those skilled in the art so that an effective amount of the active ingredient is administered to the subject, on the basis of factors such as the animal species, health condition, age, and weight of the subject, the administration route, and the employed dosage form. Those skilled in the art may easily determine the effective amount in a given situation by routine experimentation, which is within the range of ordinary skill and determination of clinicians. For example, when the active ingredient is an antisense nucleic acid, it may be administered in the range of about 0.01 to 100 mg/kg body weight, about 0.05 to 10 mg/kg body weight, or about 0.1 to 5 mg/kg body weight.

The composition may be used alone or in combination with at least one further active ingredient, especially an active ingredient for treating or preventing inflammation or a disease associated with inflammation. When some ingredients are used in combination, a dosage form containing all the ingredients or a combination of dosage forms containing the ingredients separately may be employed. The ingredients may be simultaneously or sequentially administered or any ingredient may be administered at later time point, as long as the ingredients are used for suppressing inflammation or preventing and/or treating a disease associated with inflammation. Two or more further active ingredients may be used in combination. Examples of the active ingredients suitable for use in combination include anti-inflammatory agents, antibacterial agents, antifungal agents, antiviral agents, immunosuppressive agents, and molecular target drugs.

An aspect of the disclosure provides a method of suppressing inflammation comprising administering at least one substance that disrupts a stem-loop structure in the 3' untranslated region of a Regnase-1 mRNA to a subject in need thereof.

An aspect of the disclosure provides at least one substance that disrupts a stem-loop structure in the 3' untranslated region of a Regnase-1 mRNA for use in suppressing inflammation.

An aspect of the disclosure provides use of at least one substance that disrupts a stem-loop structure in the 3' untranslated region of a Regnase-1 mRNA for suppressing inflammation.

An aspect of the disclosure provides use of at least one substance that disrupts a stem-loop structure in the 3' untranslated region of a Regnase-1 mRNA for manufacturing a pharmaceutical composition for suppressing inflammation.

An aspect of the disclosure provides a method of treating and/or preventing a disease associated with inflammation comprising administering at least one substance that disrupts a stem-loop structure in the 3' untranslated region of a Regnase-1 mRNA to a subject in need thereof.

An aspect of the disclosure provides at least one substance that disrupts a stem-loop structure in the 3' untranslated region of a Regnase-1 mRNA for use in treating and/or preventing a disease associated with inflammation.

An aspect of the disclosure provides use of at least one substance that disrupts a stem-loop structure in the 3' untranslated region of a Regnase-1 mRNA for treating and/or preventing a disease associated with inflammation.

An aspect of the disclosure provides use of at least one substance that disrupts a stem-loop structure in the 3' untranslated region of a Regnase-1 mRNA for manufacturing a pharmaceutical composition for treating and/or preventing a disease associated with inflammation.

Another aspect of the disclosure provides a method of screening for an agent for suppressing inflammation. Step (a) of the method is introducing a candidate substance to a cell expressing a Regnase-1 gene and a reporter gene, the reporter gene fused with the 3' untranslated region of a Regnase-1 mRNA.

The 3' untranslated region of the Regnase-1 mRNA is as described above. The reporter gene may be any reporter gene that directly or indirectly generates a detectable label, such as chloramphenicol acetyltransferase (CAT) gene, green fluorescent protein (GFP) gene, β-glucuronidase (GUS) gene, luciferase gene, and other marker genes. The 3' untranslated region of the Regnase-1 mRNA is linked downstream of the reporter gene. In an embodiment, the 3' untranslated region of the Regnase-1 mRNA comprises the nucleotide sequence of SEQ ID NO: 5 or 6. In an embodiment, the 3' untranslated region of the Regnase-1 mRNA comprises the nucleotide sequence of SEQ ID NO: 1 or 2.

The Regnase-1 gene means a gene encoding Regnase-1 as described above. The Regnase-1 gene may be intrinsic to the cell used in the method or may be introduced into the cell by a genetic recombination technique.

The cell used in the method may be any cell that is capable of expressing the reporter gene linked to the 3' untranslated region of the Regnase-1 mRNA and, if necessary, the Regnase-1 gene. Examples of the cells include HeLa cells, HEK293 cells, HepG2 cells, and COS-7 cells. Other necessary steps such as construction of a transfection vector and transfection may be performed by known methods (Molecular Cloning: A Laboratory Manual 2nd edition (1989), Cold Spring Harbor Laboratory Press).

The candidate substance may be any substance, for example, proteins, amino acids, nucleic acids, lipids, carbohydrates, and small molecules. The candidate substance is typically a purified or isolated substance, but may be provided in an unpurified or unisolated crude material. The candidate substance may be provided in a library, such as a compound library, a nucleic acid library, or a random peptide library, or may be provided in a natural material. The candidate substance may be designed based on the stem-loop structure in the 3' untranslated region of the Regnase-1 mRNA. The introduction of the candidate substance into the cell may be performed by a known method, depending on the type of the candidate substance.

Step (b) of the method is measuring an expression level of the reporter gene in the cell. The expression level may be measured by a known method suitable for the reporter gene.

Step (c) of the method is identifying the candidate substance as the agent for suppressing inflammation when the expression level measured in the presence of the candidate substance is higher than the expression level measured in the absence of the candidate substance. The candidate substance may be identified as the agent for suppressing inflammation when the expression level measured in the presence of the candidate substance is, e.g., at least about 10%, preferably at least about 20%, more preferably at least about 30%, even more preferably at least about 50%, higher than the expression level measured in the absence of the candidate substance.

For example, the disclosure provides the following embodiments.

[1] A composition for suppressing inflammation, comprising at least one substance that disrupts a stem-loop structure in the 3' untranslated region of a Regnase-1 mRNA.

[2] The composition according to item 1, for treating and/or preventing a disease associated with inflammation.

[3] A composition for treating and/or preventing a disease associated with inflammation, comprising at least one substance that disrupts a stem-loop structure in the 3' untranslated region of a Regnase-1 mRNA.

[4] The composition according to item 2 or 3, for treating the disease associated with inflammation.

[5] The composition according to any one of items 2 to 4, wherein the disease associated with inflammation is an autoimmune disease, septic shock, or graft rejection.

[6] The composition according to any one of items 2 to 5, wherein the disease associated with inflammation is an autoimmune disease.

[7] The composition according to item 6, wherein the autoimmune disease is multiple sclerosis, autoimmune encephalomyelitis, rheumatoid arthritis, or systemic lupus erythematosus.

[8] The composition according to item 6 or 7, wherein the autoimmune disease is multiple sclerosis.

[9] The composition according to any one of items 2 to 5, wherein the disease associated with inflammation is septic shock.

[10] The composition according to item 9, wherein the septic shock is acute respiratory distress syndrome, idiopathic pulmonary fibrosis, or interstitial pneumonia.

[11] The composition according to item 9 or 10, wherein the septic shock is acute respiratory distress syndrome.

[12] The composition according to any one of items 1 to 11, wherein the stem-loop structure is at least one stem-loop structure selected from a first stem-loop structure formed in the region corresponding to positions 231 to 245 of SEQ ID NO: and a second stem-loop structure formed in the region corresponding to positions 424 to 442 of SEQ ID NO: 1.

[13] The composition according to any one of items 1 to 12, wherein the 3' untranslated region of the Regnase-1 mRNA comprises the nucleotide sequence of SEQ ID NO: 5.

[14] The composition according to any one of items 1 to 13, wherein the 3' untranslated region of the Regnase-1 mRNA comprises the nucleotide sequence of SEQ ID NO: 1.

[15] The composition according to any one of items 1 to 14, wherein the substance that disrupts the stem-loop structure is an oligonucleotide capable of binding to the nucleotide sequence forming the stem-loop structure.

[16] The composition according to any one of items 1 to 15, wherein the substance that disrupts the stem-loop structure is
(a) a first oligonucleotide selected from
  (a-1) an oligonucleotide consisting of 10 to 30 nucleotides and being capable of binding to a sequence that consists of contiguous 10 to 30 nucleotides within positions 206 to 242 of SEQ ID NO: 1 and comprises the nucleotides at positions 233 to 235 of SEQ ID NO: 1, and
  (a-2) an oligonucleotide consisting of 10 to 30 nucleotides and being capable of binding to a sequence that consists of contiguous 10 to 30 nucleotides within positions 234 to 270 of SEQ ID NO: 1 and comprises the nucleotides at positions 241 to 243 of SEQ ID NO: 1,
(b) a second oligonucleotide selected from
  (b-1) an oligonucleotide consisting of 10 to 30 nucleotides and being capable of binding to a sequence that consists of contiguous 10 to 30 nucleotides within positions 399 to 439 of SEQ ID NO: 1 and comprises the nucleotides at positions 426 to 428 of SEQ ID NO: 1, and
  (b-2) an oligonucleotide consisting of 10 to 30 nucleotides and being capable of binding to a sequence that consists of contiguous 10 to 30 nucleotides within positions 427 to 467 of SEQ ID NO: 1 and comprises the nucleotides at positions 438 to 440 of SEQ ID NO: 1, or
(c) a combination of the first oligonucleotide and the second oligonucleotide.

[17] The composition according to any one of items 1 to 16, wherein the at least one substance that disrupts the stem-loop structure is
(a) a first oligonucleotide selected from
  (a-1) an oligonucleotide comprising a nucleotide sequence having at least 90% identity with SEQ ID NO: 7 and being capable of binding to a sequence that consists of contiguous 10 to 30 nucleotides within positions 206 to 242 of SEQ ID NO: 1 and comprises the nucleotides at positions 233 to 235 of SEQ ID NO: 1, and
  (a-2) an oligonucleotide comprising a nucleotide sequence having at least 90% identity with SEQ ID NO: 8 and being capable of binding to a sequence that consists of contiguous 10 to 30 nucleotides within positions 234 to 270 of SEQ ID NO: 1 and comprises the nucleotides at positions 241 to 243 of SEQ ID NO: 1,
(b) a second oligonucleotide selected from
  (b-1) an oligonucleotide comprising a nucleotide sequence having at least 90% identity with SEQ ID NO: 9 and being capable of binding to a sequence that consists of contiguous 10 to 30 nucleotides within positions 399 to 439 of SEQ ID NO: 1 and comprises the nucleotides at positions 426 to 428 of SEQ ID NO: 1, and
  (b-2) an oligonucleotide comprising a nucleotide sequence having at least 90% identity with SEQ ID NO: 10 and being capable of binding to a sequence that consists of contiguous 10 to 30 nucleotides within positions 427 to 467 of SEQ ID NO: 1 and comprises the nucleotides at positions 438 to 440 of SEQ ID NO: 1, or
(c) a combination of the first oligonucleotide and the second oligonucleotide.

[18] The composition according to any one of items 1 to 16, wherein the at least one substance that disrupts the stem-loop structure is
(a) a first oligonucleotide selected from
  (a-1) an oligonucleotide consisting of a nucleotide sequence that is different from the nucleotide sequence of SEQ ID NO: 7 in that one, two, or three nucleotides are deleted, substituted, added, or inserted and being capable of binding to a sequence that consists of contiguous 10 to 30 nucleotides within positions 206 to 242 of SEQ ID NO: 1 and comprises the nucleotides at positions 233 to 235 of SEQ ID NO: 1, and (a-2) an oligonucleotide consisting of a nucleotide sequence that is different from the nucleotide sequence of SEQ ID NO: 8 in that one, two, or three nucleotides are deleted, substituted, added, or inserted and being capable of binding to a sequence that consists of contiguous 10 to 30 nucleotides within positions 234 to 270 of SEQ ID NO: 1 and comprises the nucleotides at positions 241 to 243 of SEQ ID NO: 1, (b) a second oligonucleotide selected from (b-1) an oligonucleotide consisting of a nucleotide sequence that is different from the nucleotide sequence of SEQ ID NO: 9 in that one, two, or three nucleotides are deleted, substituted, added, or inserted and being capable of binding to a sequence that consists of contiguous 10 to 30 nucleotides within positions 399 to 439 of SEQ ID NO: 1 and comprises the nucleotides at positions 426 to 428 of SEQ ID NO: 1, and (b-2) an oligonucleotide consisting of a nucleotide sequence that is different from the nucleotide sequence of SEQ ID NO: 10 in that one, two, or three nucleotides are deleted, substituted, added, or inserted and being capable of binding to a sequence that consists of contiguous 10 to 30 nucleotides within positions 427 to 467 of SEQ ID NO: 1 and comprises the nucleotides at positions 438 to 440 of SEQ ID NO: 1, or (c) a combination of the first oligonucleotide and the second oligonucleotide.

[19] The composition according to any one of items 1 to 18, wherein the at least one substance that disrupts the stem-loop structure is (a) a first oligonucleotide selected from (a-1) an oligonucleotide comprising the nucleotide sequence of SEQ ID NO: 7, and (a-2) an oligonucleotide comprising the nucleotide sequence of SEQ ID NO: 8, (b) a second oligonucleotide selected from (b-1) an oligonucleotide comprising the nucleotide sequence of SEQ ID NO: 9, and (b-2) an oligonucleotide comprising the nucleotide sequence of SEQ ID NO: 10, or (c) a combination of the first oligonucleotide and the second oligonucleotide.

[20] The composition according to any one of items 1 to 19, wherein the at least one substance that disrupts the stem-loop structure is (a) a first oligonucleotide selected from (a-1) an oligonucleotide consisting of the nucleotide sequence of SEQ ID NO: 7, and (a-2) an oligonucleotide consisting of the nucleotide sequence of SEQ ID NO: 8, (b) a second oligonucleotide selected from (b-1) an oligonucleotide consisting of the nucleotide sequence of SEQ ID NO: 9, and (b-2) an oligonucleotide consisting of the nucleotide sequence of SEQ ID NO: 10, or (c) a combination of the first oligonucleotide and the second oligonucleotide.

[21] The composition according to any one of items 15 to 20, wherein the oligonucleotide consists of 10 to 30 nucleotides.

[22] The composition according to any one of items 15 to 21, wherein the oligonucleotide consists of 15 to 27 nucleotides.

[23] The composition according to any one of items 15 to 22, wherein the oligonucleotide consists of 18 to 25 nucleotides.

[24] The composition according to any one of items 15 to 23, wherein the oligonucleotide consists of 20 to 23 nucleotides.

[25] The composition according to any one of items 16 to 24, wherein the first oligonucleotide is the oligonucleotide (a-1).

[26] The composition according to any one of items 16 to 24, wherein the first oligonucleotide is the oligonucleotide (a-2).

[27] The composition according to any one of items 16 to 26, wherein the second oligonucleotide is the oligonucleotide (b-1).

[28] The composition according to any one of items 16 to 26, wherein the second oligonucleotide is the oligonucleotide (b-2).

[29] The composition according to any one of items 16 to 28, comprising the combination of the first oligonucleotide and the second oligonucleotide.

[30] A combination of the composition according to any one of items 16 to 28 that comprises the first oligonucleotide and the composition according to any one of items 16 to 28 that comprises the second oligonucleotide.

[31] The composition according to item 29 or the combination according to item 30, comprising the oligonucleotide (a-1) and the oligonucleotide (b-1).

[32] The composition according to item 29 or the combination according to item 30, comprising the oligonucleotide (a-1) and the oligonucleotide (b-2).

[33] The composition according to item 29 or the combination according to item 30, comprising the oligonucleotide (a-2) and the oligonucleotide (b-1).

[34] The composition according to item 29 or the combination according to item 30, comprising the oligonucleotide (a-2) and the oligonucleotide (b-2).

[35] A method of screening for an agent for suppressing inflammation, comprising (a) introducing a candidate substance to a cell expressing a Regnase-1 gene and a reporter gene, the reporter gene fused with the 3' untranslated region of a Regnase-1 mRNA;

(b) measuring an expression level of the reporter gene in the cell, and (c) identifying the candidate substance as the agent for suppressing inflammation when the expression level measured in the presence of the candidate substance is higher than the expression level measured in the absence of the candidate substance.

[36] A method of screening for an agent for treating and/or preventing a disease associated with inflammation, comprising (a) introducing a candidate substance to a cell expressing a Regnase-1 gene and a reporter gene, the reporter gene fused with the 3' untranslated region of a Regnase-1 mRNA;

(b) measuring an expression level of the reporter gene in the cell, and (c) identifying the candidate substance as the agent for treating and/or preventing a disease associated with inflammation when the expression level measured in the presence of the candidate substance is higher than the expression level measured in the absence of the candidate substance.

[37] The method according to item 36, wherein the disease associated with inflammation is an autoimmune disease, septic shock, or graft rejection.

[38] The method according to item 36 or 37, wherein the disease associated with inflammation is an autoimmune disease.

[39] The method according to item 38, wherein the autoimmune disease is multiple sclerosis, autoimmune encephalomyelitis, rheumatoid arthritis, or systemic lupus erythematosus.
[40] The method according to item 38 or 39, wherein the autoimmune disease is multiple sclerosis.
[41] The method according to item 36, wherein the disease associated with inflammation is septic shock.
[42] The method according to item 41, wherein the septic shock is acute respiratory distress syndrome, idiopathic pulmonary fibrosis, or interstitial pneumonia.
[43] The method according to item 41 or 42, wherein the septic shock is acute respiratory distress syndrome.
[44] The method according to any one of items 35 to 43, wherein the 3' untranslated region of the Regnase-1 mRNA comprises the nucleotide sequence of SEQ ID NO: 5.
[45] The method according to any one of items 35 to 44, wherein the 3' untranslated region of the Regnase-1 mRNA comprises the nucleotide sequence of SEQ ID NO: 1.
[46] The method according to any one of items 35 to 45, further comprising a step of designing the candidate substance based on the stem-loop structure in the 3' untranslated region of the Regnase-1 mRNA.

The entire contents of the documents cited herein are incorporated herein by reference.

The embodiments described above are non-limiting and may be modified without deviating from the scope of the invention as defined by the appended claims. The following examples are non-limiting and provided only for describing the invention.

EXAMPLES

Example 1: Identification of Stem-Loop Regions in the Mouse Regnase-1 (Zc3h12a) 3' UTR Responsible for Regnase-1-Mediated Suppression The mouse Regnase-1 (Zc3h12a) 3' UTR having the nucleotide sequence of SEQ ID NO: 2 was used. As shown in FIG. 4, pGL3 luciferase reporter plasmids (Promega) containing the indicated fragments of the non-stem-loop sequences in the 3' UTR (position 244-379 or 400-731 of SEQ ID NO: 2) or the stem-loop sequences in the 3' UTR (position 191-211 or 378-392 of SEQ ID NO: 2) followed by b-globin 3' UTR were generated.

Next, HeLa cells were transfected with the indicated pGL3 reporter plasmids together with an expression plasmid for Regnase-1 or its nuclease dead mutant (D141N) or an empty plasmid (as control). After 24 hours of cultivation, the cells were lysed and the luciferase activities in the lysates were determined with the Dual-luciferase Reporter Assay system (Promega). The gene encoding Renilla luciferase was transfected simultaneously as an internal control.

The results are shown in FIG. 4. Expression of the luciferase reporter by the plasmids containing one of the stem-loop sequences (position 191-211 or 378-392) in the Regnase-1 3' UTR was reduced when the expression plasmid for Regnase-1 was co-introduced, but not reduced when the expression plasmid for D141N was co-introduced. Expression of the luciferase reporter by the plasmids containing one of the non-stem-loop sequences (position 244-379 or 400-731) in the Regnase-1 3' UTR was not reduced when the expression plasmid for Regnase-1 or the expression plasmid for D141N was co-introduced. The results suggest that Regnase-1 recognizes the stem-loop structures in the 3' UTR of a Regnase-1 mRNA and degrades the Regnase-1 mRNA.

Example 2: Morpholino Oligos (MOs) Targeting the Stem-Loops of the Regnase-1 3' UTR Increase the Luciferase Activity of the Luciferase Reporter Plasmid Harboring the Mouse Regnase-1 3' UTR HEK293 cells were transfected with the pGL3 luciferase reporter plasmid harboring the full length mouse Regnase-1 3' UTR together with the MOs (GeneTools) indicated in FIG. 5 by using Endo-Porter (GeneTools). The cells were harvested 24 hours after the transfection, and the luciferase activities in the lysates were determined with the Dual-luciferase Reporter Assay system (Promega). The gene encoding Renilla luciferase was transfected simultaneously as an internal control.

The MOs had the following nucleotide sequences; the nucleotide sequence of 191-210MO was complementary to the nucleotide sequence at positions 201 to 223 of SEQ ID NO: 2 (the nucleotide sequence of the mouse Regnase-1 3' UTR) and the nucleotide sequence of 378-392MO was complementary to the nucleotide sequence at positions 384 to 403 of SEQ ID NO: 2.

TABLE 1

| 191-210MO | 5'-CTTAAATGACAGAGATACAATGT-3' | SEQ ID NO: 12 |
|---|---|---|
| 378-392MO | 5'-CCTCAGAGAGCAGGCACATG-3' | SEQ ID NO: 14 |

Figure 5:
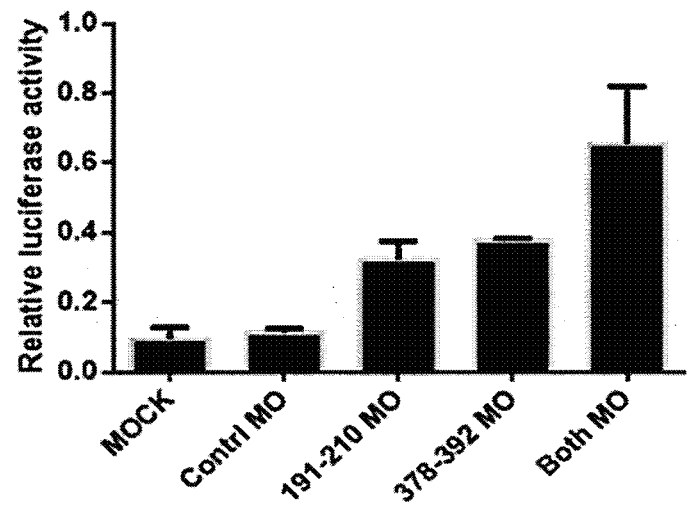
FIG. 5 shows the results of the reporter assay using a luciferase reporter plasmid harboring the full length 3' UTR of a mouse Regnase-1 mRNA in the presence of morpholino oligos (MOs) targeting the stem-loops in the 3' UTR of the Regnase-1 mRNA.

The results are shown in FIG. 5. The luciferase activity was higher when the reporter plasmid was introduced to the cells simultaneously with 191-210MO or 378-392MO than introduced with no MO (MOCK) or control MO. The luciferase activity was even higher when both 191-210MO and 378-392MO (Both MO) were introduced. The results indicate that disruption of the stem-loop structures in the 3' UTR of a Regnase-1 mRNA suppresses degradation of the Regnase-1 mRNA by Regnase-1. The results also suggest that the two stem-loop structures are independently recognized by Regnase-1.

Example 3: Treatment of Mouse Bone Marrow Macrophages (BMMs) with MOs and Measurement of mRNA Levels of Cytokines and Regnase-1

(A) BMMs were seeded on a 12-well plate and transfected with 191-210MO and 378-392MO (2 μM/MO) as described in Example 2 by using 6 μl/well of Endo-Porter (GeneTools, LLC). After 24 hours, the cells were treated with LPS (10 ng/ml) or TNFα (10 ng/ml) for 2 hours. The cells were then harvested for RNA extraction. The mRNA levels of IL-6, TNFα, IL-1β, and Regnase-1 were measured by QPCR analysis.

(B) The BMMs which were treated with the MOs and then treated with LPS or TNFα as described above were lysed and the levels of Regnase-1 were determined by Western blotting using an anti-Regnase-1 antibody.

Results are shown in FIG. 6. The mRNA levels of IL-6, TNFα, and IL-1β were increased by the LPS treatment, and the increase was suppressed by the MOs targeting the stem-loop sequences in the Regnase-1 3' UTR. On the other hand, the Regnase-1 mRNA level was increased by the MO treatment and the LPS treatment. The expression of Regnase-1 in the BMMs treated with LPS or TNFα for 2 hours was also increased by the MO treatment. The results suggest that the Regnase-1-mediated degradation of the Regnase-1 mRNA was suppressed by the MOs, which leaded the increase in the amount of Regnase-1 and the enhancement of the Regnase-1-mediated degradation of the IL-6, TNFα, and IL-1β mRNAs.

Example 4: Effects of Intratracheal MO Treatment in LPS-Induced Acute Respiratory Distress Syndrome (ARDS) Mouse Model Mice were anesthetized by intraperitoneal injection of pentobarbital. The mice were intratracheally treated with vivo-morpholino oligos (MOs) (GeneTools) at 25 µg/MO/head (20 µl/injection). The vivo-MOs had the same nucleotide sequences as 191-210MO and 378-392MO described in Example 2. After 24 hours, the mice were anesthetized again by intraperitoneal injection of pentobarbital and intratracheally treated with LPS (10 µg/20 µl PBS; phosphate-buffered saline). After 8 hours, the mice were sacrificed. For analysis of RNAs, lung samples were kept in RNAlater (Qiagen) at −80° C. until use. RNA samples were prepared by Trizol (Thermo Fisher Scientific) and the mRNA levels of IL-6, TNFα, IL-1β, and Regnase-1 were measured by QPCR analysis.

Figure 7:
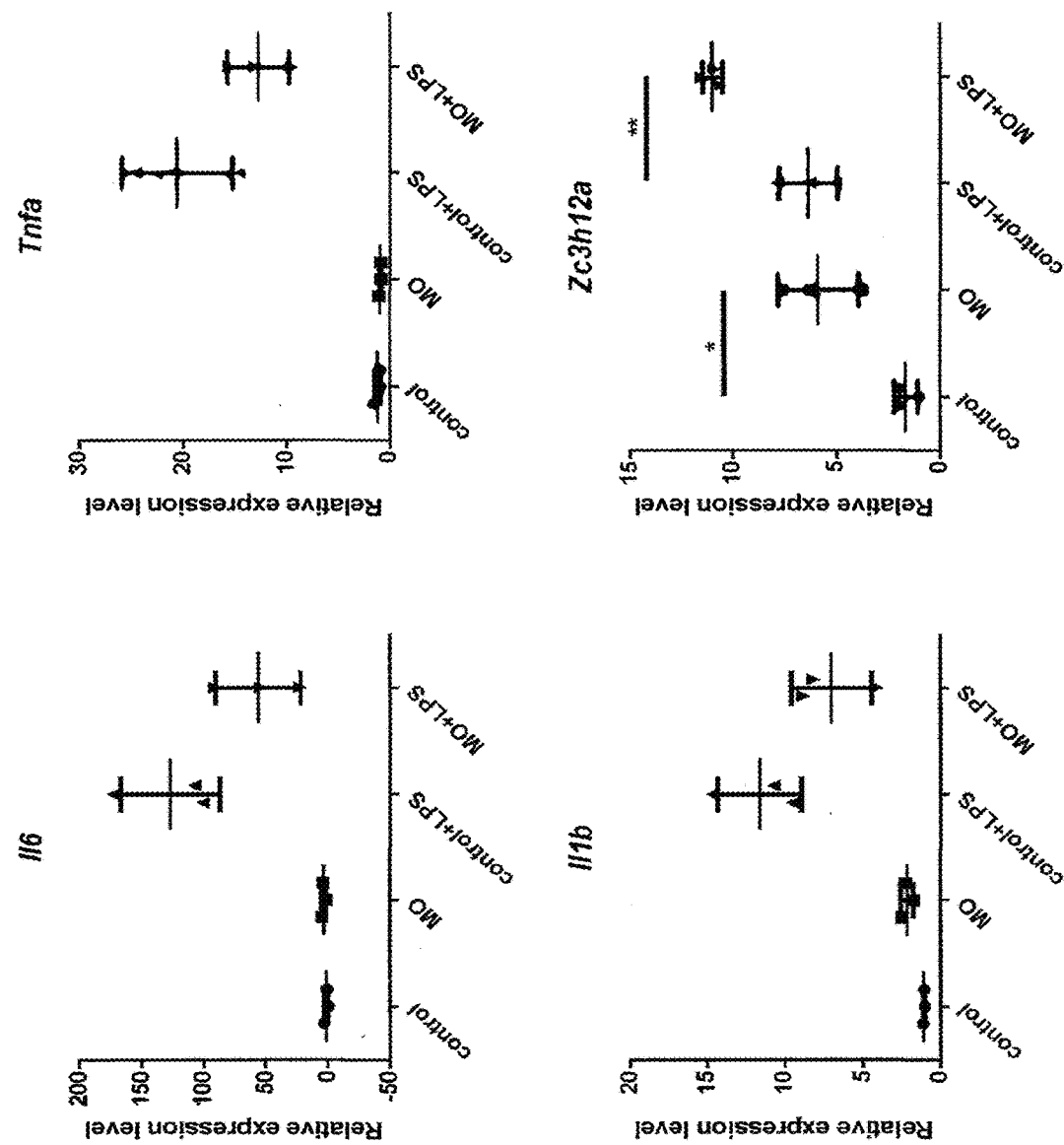
FIG. 7 shows the mRNA levels of the cytokines and Regnase-1 in lung tissues of mice treated with MOs and LPS via intratracheal administration.

The results are shown in FIG. 7. Mice affected by acute lung injuries due to intratracheal LPS administration can be used as a model for ARDS. The mRNA levels of IL-6, TNFα, and IL-1β were increased by the LPS treatment, and the increase was suppressed by the MOs targeting the stem-loop sequences in the Regnase-1 3' UTR. On the other hand, the Regnase-1 mRNA level was increased by the MO treatment or the LPS treatment, and further increased by the combination of the MO and LPS treatments. The results suggest that the Regnase-1-mediated degradation of the Regnase-1 mRNA was inhibited in vivo by the MOs, which leaded the increase in the amount of Regnase-1 and the enhancement of the Regnase-1-mediated degradation of the IL-6, TNFα, and IL-1β mRNAs.

Example 5: Effects of Intracranial MO Treatment in Experimental Autoimmune Encephalomyelitis (EAE) Mice Myelin Oligodendrocyte Glycoprotein (MOG) peptide (35-55) (ANASPEC Inc) was diluted to the concentration of 2 µg/µL in PBS. Complete Freund's Adjuvant (Sigma) and the diluted MOG were mixed at the ratio of 1:1 in a 1.5 mL Eppendorf tube. Emulsion was generated by sonication using a microtip-fitted sonicator. The completion of the emulsion formation was confirmed by dropping a drop of the emulsion on the water surface in a beaker and observing the drop sank without diffusing. When the formation was incomplete, the tube was cooled for 2-3 minutes on ice and the sonication was repeated. For immunizing each mouse 200 µL of the emulsion was used.

Each mouse was immunized with subcutaneous injections at two locations (100 µL/bolus) between the front limbs and between the hind limbs on the back side. To each mouse 200 ng of 1 ng/µL PTx (Sigma) was intraperitoneally administered. Another 200 ng of PTx was intraperitoneally administered 48 hours after the first injection.

The mice were anesthetized by intraperitoneal injection of pentobarbital 10 days after the immunization. The hair on the head was removed by a hair clipper and hair removal cream. The bregma was located and 7 µg/MO/head of the two vivo-morpholino oligos described in Example 4 (10 µL/injection) or PBS were intracranially injected to the 1 mm right or left side of the bregma (n=10). Recording of the body weights and clinical symptom scores (EAE scores) was initiated 7 days after the immunization by the MOG peptide and continued daily.

Figure 8:
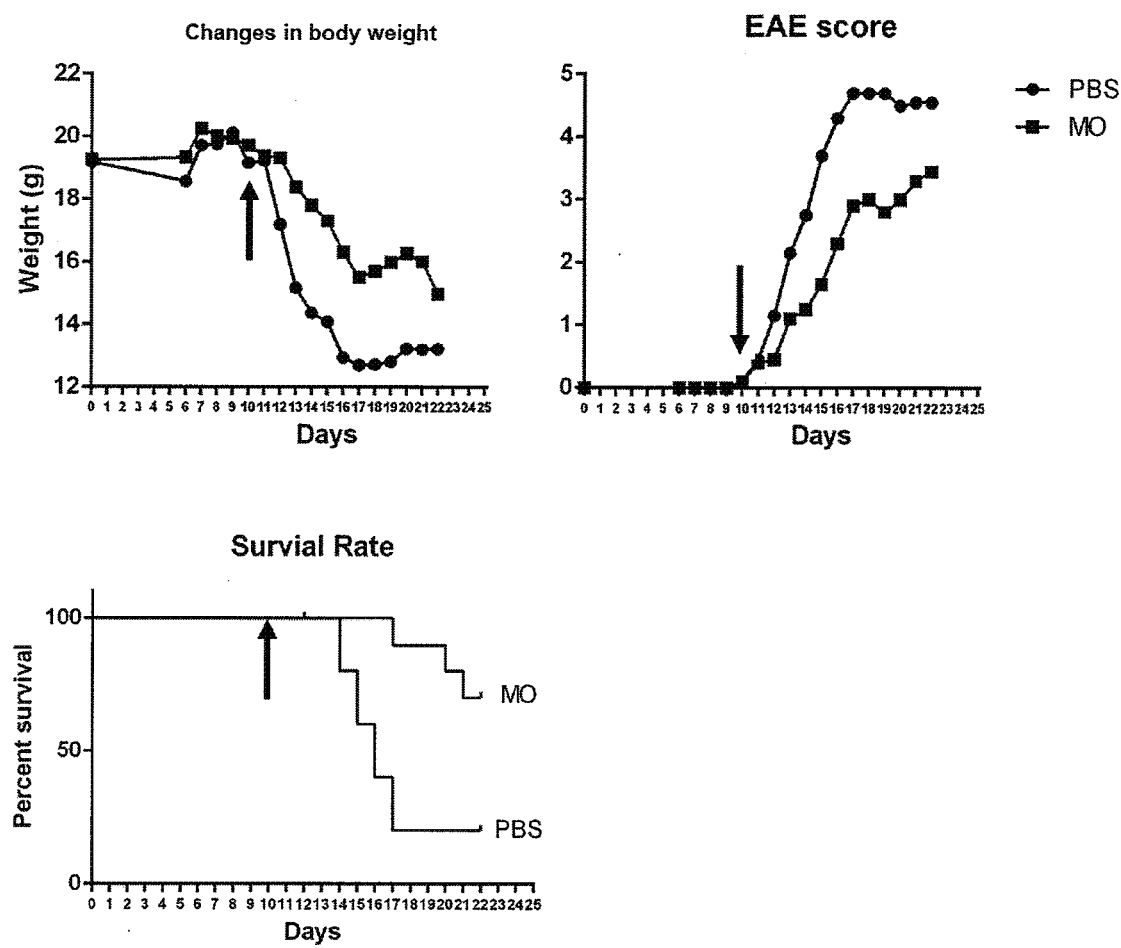
FIG. 8 shows the effects of intracranially administrated MOs on the body weights, EAE scores, and survival rates of experimental autoimmune encephalomyelitis (EAE) mice.

The results of the body weight, clinical symptom score (EAE scores) and survival rate are shown in FIG. 8. The mice having induced autoimmune encephalomyelitis are known as an established model for multiple sclerosis. Following the immunization the EAE mice had lower body weights and increased clinical symptom scores, which indicate the severity of EAE symptoms, but the both were suppressed by the MOs targeting the stem-loop sequences in the Regnase-1 3' UTR. In addition, the survival rates of the MO-treated EAE mice were higher. The results suggest that inhibition of the stem-loop formation in a Regnase-1 3' UTR could treat autoimmune encephalomyelitis and multiple sclerosis.

Example 6: Effects of Morpholino Oligos Targeting Human Regnase-1 on LPS-Induced Cytokine Gene Expressions in Human Macrophage Cell Line THP-1 Generated by PMA (Phorbol-Myristate-Acetate)-Induced Differentiation Cells of THP-1, a human monocyte-like cell line, were seeded on a 12-well plate and treated with PMA (5 ng/ml) for 48 hours to induce macrophage differentiation. The cells were transfected with 231-245MO and 424-442MO (2 µM/MO) as shown in Table 2 by using 6 µl/well of Endo-Porter (Gene Tools, LLC). After 24 hours, the cells were treated with LPS (100 ng/ml) for 4 hours. The cells were then harvested for RNA extraction. The mRNA levels of human IL-6, TNFα, IL-1β, and Regnase-1 (Zc3h12a) were measured by QPCR analysis.

The MOs had the following nucleotide sequences; the nucleotide sequence of 231-245MO was complementary to the nucleotide sequence at positions 236 to 258 of SEQ ID NO: 1 (the nucleotide sequence of the human Regnase-1 3' UTR) and the nucleotide sequence of 424-442MO was complementary to the nucleotide sequence at positions 414 to 432 of SEQ ID NO: 1.

TABLE 2

| | | |
|---|---|---|
| 231-245MO | 5'-CTTAAACTACAGAGATACAATGT-3' | SEQ ID NO: 8 |
| 424-442MO | 5'-ACGGTGCCCAACTAGCCAG-3' | SEQ ID NO: 9 |

Figure 9:
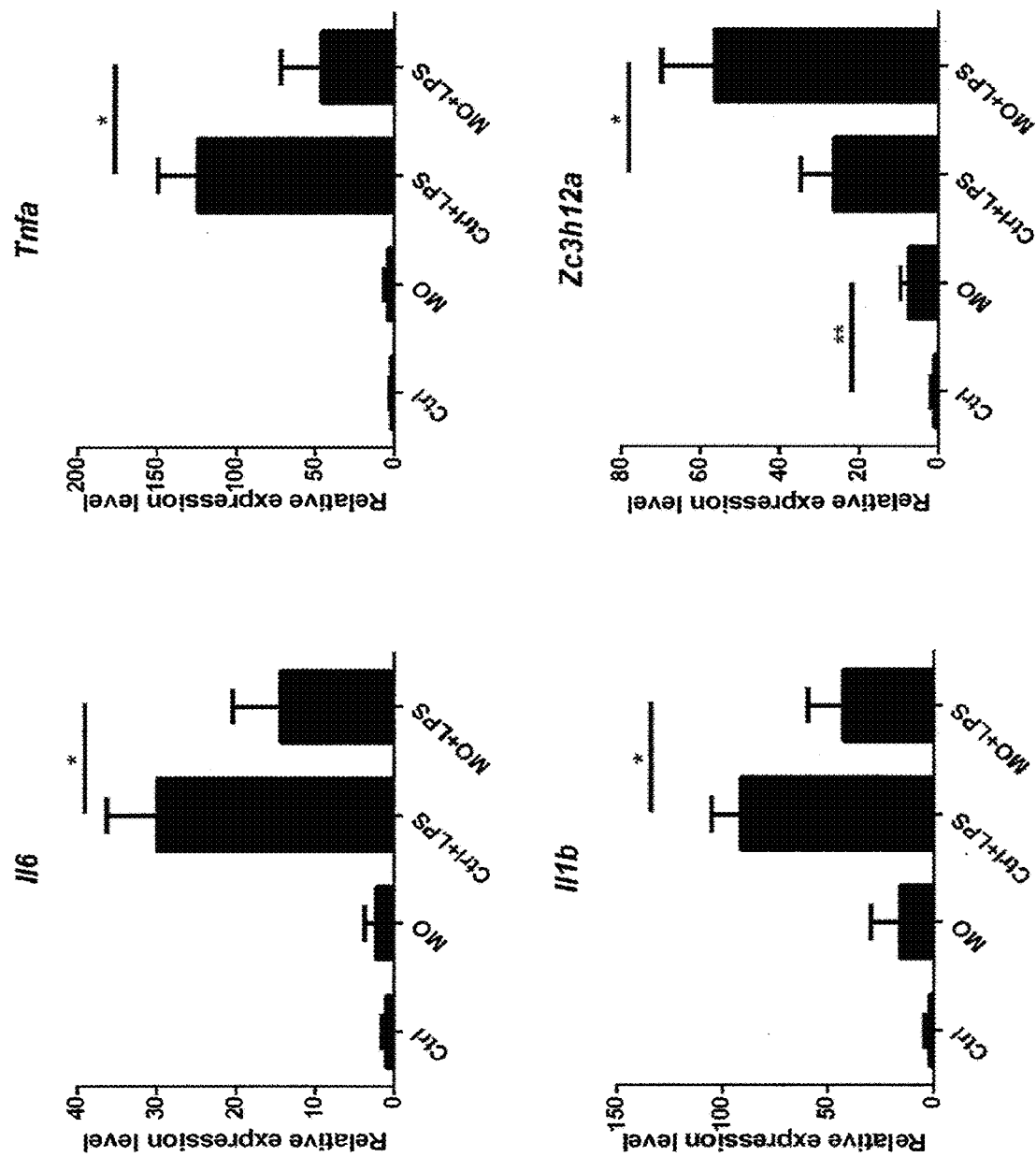
FIG. 9 shows the mRNA levels of the cytokines and Regnase-1 after LPS treatment in human THP-1 cells treated with MOs.

The results are shown in FIG. 9. The mRNA levels of IL-6, TNFα, and IL-1β were increased by the LPS treatment, and the increase was suppressed by the MOs targeting the stem-loop sequences in the Regnase-1 3' UTR. On the other hand, the Regnase-1 mRNA level was increased by the MO treatment or the LPS treatment, and further increased by the combination of the MO and LPS treatments. The results suggest that the Regnase-1-mediated degradation of the Regnase-1 mRNA was inhibited by the MOs even in human cells, which leaded the increase in the amount of Regnase-1 and the enhancement of the Regnase-1-mediated degradation of the IL-6, TNFα, and IL-1β mRNAs.

Example 7

THP-1 cells were seeded on a 12-well plate and transfected with DNA oligonucleotides 191-210ASO and 378-

392ASO having the nucleotide sequences shown in Table 1 by using Lipofectamin 2000. After 48 hours, the cells were treated with LPS (100 ng/ml) for 4 hours. The cells were then harvested for RNA extraction. The mRNA levels of human IL-6, TNFα, IL-1β, Ptgs2 (prostaglandin-endoperoxide synthase 2), and Regnase-1 (Zc3h12a) were measured by QPCR analysis.

Figure 10:
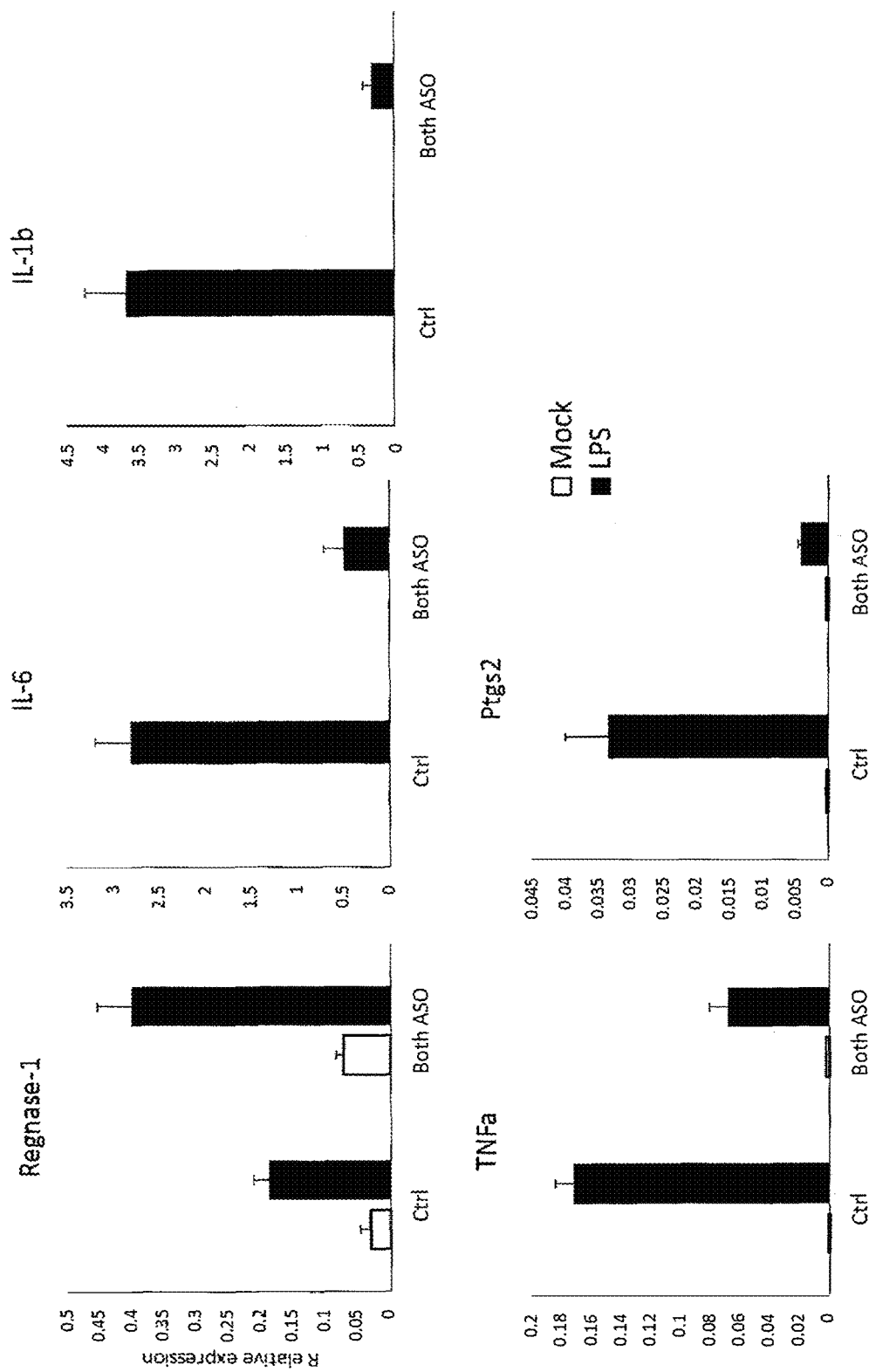
FIG. 10 shows the mRNA levels of the cytokines and Regnase-1 after LPS treatment in human THP-1 cells treated with antisense oligo DNAs (ASOs).

The results are shown in FIG. 10. The mRNA levels of IL-6, TNFα, IL-1β, and Ptgs2 were increased by the LPS treatment, and the increase was suppressed by the ASOs targeting the stem-loop sequences in the Regnase-1 3' UTR. On the other hand, the Regnase-1 mRNA level was increased by the ASO treatment or the LPS treatment, and further increased by the combination of the ASO and LPS treatments. The results suggest that the Regnase-1-mediated degradation of the Regnase-1 mRNA was inhibited by the ASOs, like the MOs, which leaded the increase in the amount of Regnase-1 and the enhancement of the Regnase-1-mediated degradation of the IL-6, TNFα, IL-1β, and Ptgs2 mRNAs.

INDUSTRIAL APPLICABILITY

The disclosure provides a method for suppressing inflammation by using the 3' UTR-mediated autosuppressing mechanism of Regnase-1. The mechanism of action has been found for the first time and the method has the potential to treat diseases that cannot be treated by existing therapies. More effective therapies could be developed by combining the method with conventional therapies.

What is claimed is:

1. A substance that disrupts a stem-loop structure in the 3' untranslated region of a Regnase-1 mRNA,
wherein the stem-loop structure is at least one stem-loop structure selected from a first stem-loop structure formed in a region corresponding to positions 231 to 245 of SEQ ID NO: 1 and a second stem-loop structure formed in a region corresponding to positions 424 to 442 of SEQ ID NO: 1,
wherein the substance comprises at least one artificial nucleotide.

2. The substance according to claim 1, wherein the 3' untranslated region of the Regnase-1 mRNA comprises the nucleotide sequence of SEQ ID NO: 5.

3. The substance according to claim 1, wherein the substance that disrupts the stem-loop structure comprises:
(a) a first oligonucleotide selected from
(a-1) an oligonucleotide consisting of 10 to 30 nucleotides and being capable of binding to a sequence that consists of contiguous 10 to 30 nucleotides within positions 206 to 242 of SEQ ID NO: 1 and comprises the nucleotides at positions 233 to 235 of SEQ ID NO: 1, and
(a-2) an oligonucleotide consisting of 10 to 30 nucleotides and being capable of binding to a sequence that consists of contiguous 10 to 30 nucleotides within positions 234 to 270 of SEQ ID NO: 1 and comprises the nucleotides at positions 241 to 243 of SEQ ID NO: 1,
(b) a second oligonucleotide selected from
(b-1) an oligonucleotide consisting of 10 to 30 nucleotides and being capable of binding to a sequence that consists of contiguous 10 to 30 nucleotides within positions 399 to 439 of SEQ ID NO: 1 and comprises the nucleotides at positions 426 to 428 of SEQ ID NO: 1, and
(b-2) an oligonucleotide consisting of 10 to 30 nucleotides and being capable of binding to a sequence that consists of contiguous 10 to 30 nucleotides within positions 427 to 467 of SEQ ID NO: 1 and comprises the nucleotides at positions 438 to 440 of SEQ ID NO: 1,
or
(c) a combination of the first oligonucleotide and the second oligonucleotide.

4. The substance according to claim 1, wherein the substance that disrupts the stem-loop structure comprises:
(a) a first oligonucleotide selected from
(a-1) an oligonucleotide comprising a nucleotide sequence having at least 90% identity with SEQ ID NO: 7 and being capable of binding to a sequence that consists of contiguous 10 to 30 nucleotides within positions 206 to 242 of SEQ ID NO: 1 and comprises the nucleotides at positions 233 to 235 of SEQ ID NO: 1, and
(a-2) an oligonucleotide comprising a nucleotide sequence having at least 90% identity with SEQ ID NO: 8 and being capable of binding to a sequence that consists of contiguous 10 to 30 nucleotides within positions 234 to 270 of SEQ ID NO: 1 and comprises the nucleotides at positions 241 to 243 of SEQ ID NO: 1,
(b) a second oligonucleotide selected from
(b-1) an oligonucleotide comprising a nucleotide sequence having at least 90% identity with SEQ ID NO: 9 and being capable of binding to a sequence that consists of contiguous 10 to 30 nucleotides within positions 399 to 439 of SEQ ID NO: 1 and comprises the nucleotides at positions 426 to 428 of SEQ ID NO: 1, and (b-2) an oligonucleotide comprising a nucleotide sequence having at least 90% identity with SEQ ID NO: 10 and being capable of binding to a sequence that consists of contiguous 10 to 30 nucleotides within positions 427 to 467 of SEQ ID NO: 1 and comprises the nucleotides at positions 438 to 440 of SEQ ID NO: 1,
or
(c) a combination of the first oligonucleotide and the second oligonucleotide.

5. The substance according to claim 1, wherein the substance that disrupts the stem-loop structure comprises the combination of the first oligonucleotide and the second oligonucleotide.

6. The substance according to claim 1, wherein the substance that disrupts the stem-loop structure comprises:
(a) a first oligonucleotide selected from
(a-1) an oligonucleotide comprising the nucleotide sequence of SEQ ID NO: 7, and
(a-2) an oligonucleotide comprising the nucleotide sequence of SEQ ID NO: 8,
(b) a second oligonucleotide selected from
(b-1) an oligonucleotide comprising the nucleotide sequence of SEQ ID NO: 9, and
(b-2) an oligonucleotide comprising the nucleotide sequence of SEQ ID NO: 10,
or
(c) a combination of the first oligonucleotide and the second oligonucleotide.

7. A method of suppressing inflammation in a subject in need thereof, comprising administering the substance according to claim 1 to the subject.

8. A method of treating a disease associated with inflammation in a subject in need thereof, comprising administering the substance according to claim 1 to the subject.

9. The method according to claim 8, wherein the disease associated with inflammation is an autoimmune disease, septic shock, or graft rejection.

10. The method according to claim 8, wherein the disease associated with inflammation is multiple sclerosis, autoimmune encephalomyelitis, rheumatoid arthritis, or systemic lupus erythematosus.

11. The method according to claim 8, wherein the disease associated with inflammation is multiple sclerosis.

12. The method according to claim 8, wherein the disease associated with inflammation is acute respiratory distress syndrome, idiopathic pulmonary fibrosis, or interstitial pneumonia.

13. The method according to claim 8, wherein the disease associated with inflammation is acute respiratory distress syndrome.

14. The method according to claim 8, wherein the disease associated with inflammation is graft rejection.

15. The substance according to claim 1, wherein the artificial nucleotide comprises at least one modification selected from the group consisting of: abasic nucleosides, arabinonucleosides, 2'-deoxyuridine, α-deoxyribonucleosides, β-L-deoxyribonucleosides, peptide nucleic acids, phosphonic ester nucleic acids, locked nucleic acids, 2-O,4'-C-ethylene-bridged nucleic acids, constrained ethyl nucleosides, morpholino nucleic acids, an artificial nucleotide having a sugar modification selected from 2'-o-methylribose, 2'-o-methoxyethylribose, 2'-deoxy-2'-fluororibose, 3'-o-methylribose, 1',2'-deoxyribose, arabinose, substituted arabinoses, hexoses, and alpha-anomers, and an artificial nucleotide having a modified base selected from 5-hydroxycytosine, 5-ethylcytosine, 5-fluorouracil, or 4-thiouracil, 6-methyladenine, and 6-thioguanosine.

16. The substance according to claim 1, wherein the artificial nucleotide comprises a morpholino nucleic acid.

17. A substance comprising at least one sequence selected from the group consisting of (a-1) an oligonucleotide having at least 85% sequence identity to the nucleotide sequence of SEQ ID NO:7, (a-2) an oligonucleotide having at least 85% sequence identity to the nucleotide sequence of SEQ ID NO:8, (b-1) an oligonucleotide having at least 85% sequence identity to the nucleotide sequence of SEQ ID NO:9, and (b-2) an oligonucleotide having at least 85% sequence identity to the nucleotide sequence of SEQ ID NO:10.

* * * * *